US 012161561B2

(12) United States Patent
Arcos et al.

(10) Patent No.: US 12,161,561 B2
(45) Date of Patent: Dec. 10, 2024

(54) INTERVERTEBRAL DEVICES

(71) Applicant: AXIS SPINE TECHNOLOGIES LTD, St. Albans (GB)

(72) Inventors: Jonathan Arcos, St. Albans (GB); Christopher Reah, St. Albans (GB); Nicholas Sandham, London (GB); David Powell, London (GB)

(73) Assignee: AXIS SPINE TECHNOLOGIES LTD, Reading (GB)

( * ) Notice: Subject to any disclaimer, the term of this patent is extended or adjusted under 35 U.S.C. 154(b) by 145 days.

(21) Appl. No.: 17/794,254

(22) PCT Filed: Jan. 21, 2021

(86) PCT No.: PCT/GB2021/050135
§ 371 (c)(1),
(2) Date: Jul. 20, 2022

(87) PCT Pub. No.: WO2021/148794
PCT Pub. Date: Jul. 29, 2021

(65) Prior Publication Data
US 2023/0049680 A1 Feb. 16, 2023

(30) Foreign Application Priority Data

Jan. 21, 2020 (GB) ..................... 2000890

(51) Int. Cl.
*A61F 2/44* (2006.01)
*A61F 2/28* (2006.01)
(52) U.S. Cl.
CPC .... *A61F 2/4455* (2013.01); *A61F 2002/2835* (2013.01)
(58) Field of Classification Search
CPC ...... A61F 2/442; A61F 2/4425; A61F 2/4455; A61F 2002/443
(Continued)

(56) References Cited

U.S. PATENT DOCUMENTS 9,585,765 B2 3/2017 Niemiec et al.
2007/0270968 A1* 11/2007 Baynham .............. A61F 2/447
623/17.11
(Continued)

FOREIGN PATENT DOCUMENTS

CN 203988508 12/2014
WO 2009002975 A 12/2008
WO 2012/003175 1/2012

OTHER PUBLICATIONS

International Search Report issued in priority PCT filing PCT/GB2021/050135, mailed/published May 20, 2021.
(Continued)

*Primary Examiner* — Eduardo C Robert
*Assistant Examiner* — Christina Negrellirodriguez
(74) *Attorney, Agent, or Firm* — LIU & LIU

(57) ABSTRACT

An anterior lumbar interbody fusion device comprising a superior component, an inferior component, and a locking mechanism. The superior component bottom side and the inferior component top side oppose each other when these are received in the intervertebral space whereby their external sides abut against the respective vertebra, thereby coupling force between the latter. The components inter-engage with each other whereby they are constrained to move in an anterior-posterior direction relative to each other and resistance is presented to movement relative to each other in each of a direction of separation and a direction orthogonal to the anterior-posterior direction and to the direction of separation. The locking mechanism allows for relative movement of the components in the anterior-posterior direction which increases an extent of their overlap and presents resistance to movement of the at least one of the component in the anterior-posterior direction which decreases an extent of their overlap, for instance with a mechanism such as protrusions shaped to engage with set of recesses and sprung (Continued)

cantilever beams forming a ratchet mechanism. Optionally, the fusion device may comprise or lack a core component received between said superior and inferior components.

20 Claims, 8 Drawing Sheets

(58) Field of Classification Search
USPC .......................................... 623/17.11–17.16
See application file for complete search history.

(56) References Cited

U.S. PATENT DOCUMENTS

| | | |
|---|---|---|
| 2010/0070036 A1* | 3/2010 | Implicito .............. A61F 2/4611 606/191 |
| 2013/0085573 A1 | 4/2013 | Lemoine et al. |
| 2013/0325071 A1 | 12/2013 | Niemiec et al. |
| 2014/0207235 A1 | 7/2014 | Drapeau |
| 2014/0228957 A1 | 8/2014 | Niemiec et al. |
| 2015/0164494 A1 | 6/2015 | Glazer |
| 2015/0320568 A1 | 11/2015 | Ameil et al. |
| 2016/0250035 A1* | 9/2016 | de Villiers .............. A61F 2/442 623/17.15 |
| 2018/0036141 A1 | 2/2018 | O'Neil et al. |

OTHER PUBLICATIONS

Stryker Spine 'surgical technique' publication re "Aero-LL Laterial Lumbar Interbody and Fixation System"; Publication No. MIALL-ST-1_Rev-2_12194 (Dec. 2016).

* cited by examiner

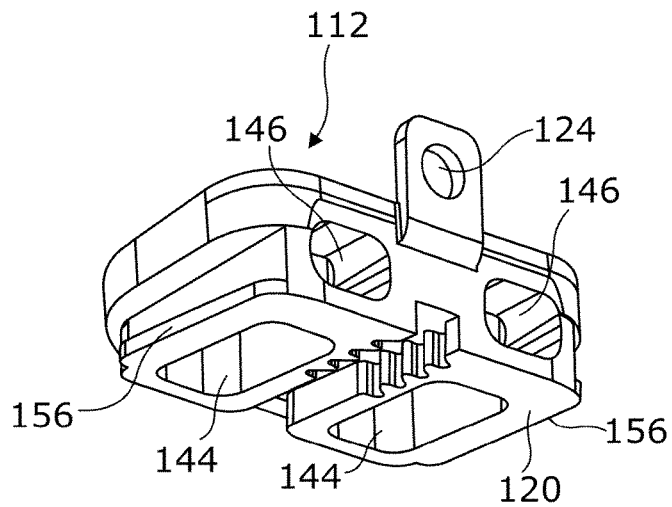
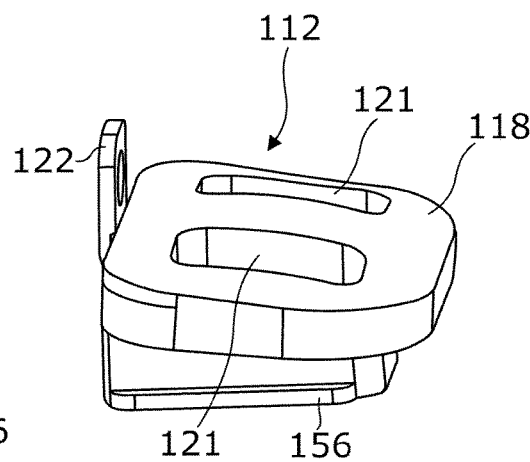
Figure 2A
Figure 2B
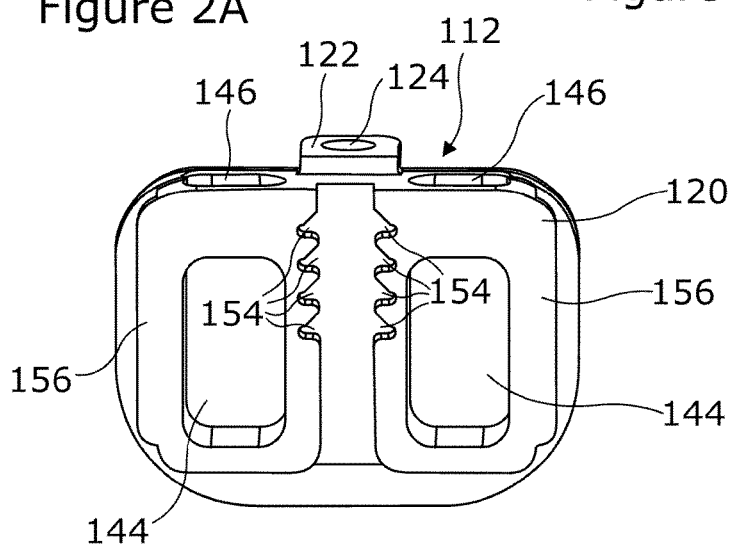
Figure 2C
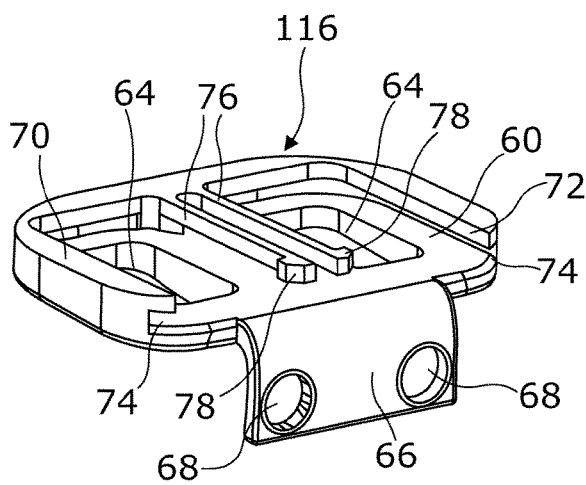
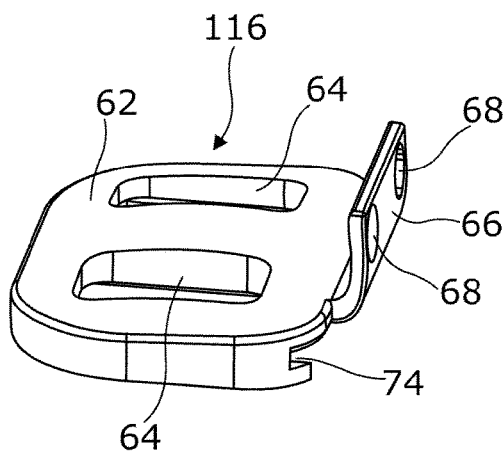
Figure 2D
Figure 2E

INTERVERTEBRAL DEVICES

FIELD OF THE INVENTION

The present invention relates to intervertebral devices and more specifically to intervertebral fusion devices.

BACKGROUND ART

Adjacent vertebrae in the spinal column are coupled to each other by a number of ligaments and the intervertebral disc. These anatomic structures hold the adjacent vertebrae together while allowing motion. Among these structures, the intervertebral disc functions as a cushion between the vertebrae whilst allowing for relative movement of the vertebrae. Problems arise from one or more of a range of diseases and conditions. One such problem is spondylolisthesis, which is a slipping out of alignment of at least one vertebra and which occurs, in most cases, at the base of the spine. The misalignment is usually in the anterior-posterior direction. Spondylolisthesis is caused by degeneration of the discs or the supporting ligaments, a defect in or fracture of at least one of both wing-shaped parts of a vertebra, developmental problems or trauma to the pars.

A first known approach to addressing spondylolisthesis involves use of pedicle screws alone. This approach is normally used when the intervertebral disc has not been compromised to the extent that there is need to restore foraminal height. In this approach pedicle screws are placed above and below the affected part of the spine. The surgeon then manipulates the spine to address the spondylolisthesis. When the surgeon is satisfied with his or her spinal manipulation, two laterally spaced apart rods are connected to the pedicle screws whereby each rod extends along the spine with the object of the thus installed rods being maintenance of the disposition of the vertebrae as set by the surgeon's manipulation of the spine. This approach often reduces but fails to eliminate the spondylolisthesis aside from requiring a fair degree of skill from the surgeon.

A second known approach to addressing spondylolisthesis involves use of pedicle screws in combination with a posterior lumbar interbody fusion (PLIF) device. This approach is normally used when the intervertebral disc has been compromised such that there is need to restore foraminal height. A PLIF device of desired height but typically of small lateral and anterior-posterior extent is used. As the name suggests, the PLIF device is inserted by the surgeon from the posterior side of the patient with the inserted PLIF device not being held in place in the intervertebral space by pins or screws. Pedicle screws are then brought into use, as described above, with the surgeon carrying out his or her spondylolisthesis addressing manipulation before the rods are connected to the pedicle screws to maintain the disposition of the vertebrae as set by the surgeon's manipulation. In common with the first approach, this second approach often reduces but fails to eliminate the spondylolisthesis aside from requiring a fair degree of skill from the surgeon.

A third known approach to addressing spondylolisthesis involves use of an anterior lumbar interbody fusion (ALIF) device and perhaps also pedicle screws. In common with the second approach, this approach is normally used when the intervertebral disc has been compromised such that there is need to restore foraminal height. An ALIF device of desired height is inserted into the intervertebral space from the anterior side of the patient. The surgeon then manipulates the spine to address the spondylolisthesis. When the desired relative disposition of vertebrae has been achieved by manipulation, the surgeon may hold the ALIF device in place by pinning or screwing the ALIF device to the adjacent vertebrae. Pedicle screws may also be used to maintain the disposition of the vertebrae as set by the surgeon's manipulation; pedicle screws are typically used where the ALIF device is not pinned or screwed to adjacent vertebrae. In common with the first and second approaches, this third approach often reduces but fails to eliminate the spondylolisthesis aside from requiring a fair degree of skill from the surgeon.

A fourth known approach to addressing spondylolisthesis is a combined of anterior and posterior procedures. In common with the second and third approaches, this approach is normally used when the intervertebral disc has been compromised such that there is need to restore foraminal height. An ALIF device of desired height is inserted into the intervertebral space from the anterior side of the patient. The ALIF device is fixed to the inferior vertebra only of the adjacent vertebra. This provides initial correction of the spondylolisthesis as well as restoring foraminal height. The patient is then turned over to gain access to the posterior side of the patient. Pedicle screws are then put in place, as described above according to the first approach, while the surgeon pulls the spine to thereby slide the superior vertebra over the ALIF device to provide further correction of the spondylolisthesis. Although this approach demands a lower level of skill from the surgeon than the previous approaches, it is not always possible to slide the superior vertebra readily over the ALIF device to achieve the desired correction.

The present inventors have become appreciative of shortcomings of known procedures for correcting spondylolisthesis, such as the shortcomings mentioned above. The present invention has been devised in light of the inventors' appreciation of such shortcomings. It is therefore an object for the present invention to provide an improved anterior lumbar interbody fusion device which provides for spondylolisthesis correction. It is a further object for the present invention to provide an improved method of correcting spondylolisthesis using an anterior lumbar interbody fusion device.

STATEMENT OF INVENTION

According to a first aspect of the present invention there is provided an anterior lumbar interbody fusion device receivable in an intervertebral space between first and second vertebrae, the anterior lumbar interbody fusion device comprising:
  a superior component having a superior component top side and a superior component bottom side, the superior component configured to be received in the intervertebral space whereby the superior component top side abuts against the first vertebra;
  an inferior component having an inferior component top side and an inferior component bottom side, the inferior component configured to be received in the intervertebral space whereby the inferior component bottom side abuts against the second vertebra, the superior component bottom side and the inferior component top side opposing each other when the superior and inferior components are received in the intervertebral space; and
  a locking mechanism, wherein
  the superior and inferior components inter-engage with each other whereby: at least a part of one of the superior and inferior components is constrained to move in an anterior-posterior direction relative to the other of the superior and inferior components; and resistance is presented to movement of the at least a part of one of the superior and inferior components relative to the other of the superior and inferior components in each of a direction of separation of the superior and inferior components and a direction orthogonal to the anterior-posterior direction and to the direction of separation, each of: the at least a part of one of the superior and inferior components; and the other of the superior and inferior components is configured to engage with its respective vertebra whereby force is coupled between it and its respective vertebra, and the locking mechanism allows for movement of the at least a part of one of the superior and inferior components in the anterior-posterior direction which increases an extent of overlap of the at least a part of one of the superior and inferior components and the other of the superior and inferior components and presents resistance to movement of the at least a part of one of the superior and inferior components in the anterior-posterior direction which decreases an extent of overlap of the at least a part of one of the superior and inferior components and the other of the superior and inferior components.

The anterior lumbar interbody fusion device, which is commonly known as an ALIF device, comprises a superior component, an inferior component and a locking mechanism. The anterior lumbar interbody fusion device is introduced into a patient's intervertebral space from the anterior side of the patient. As described further below, the locking mechanism may in part be integrally formed with one of the superior and inferior components and more specifically with the other of the superior and inferior components. The anterior lumbar interbody fusion device is receivable in an intervertebral space between first and second vertebrae.

The superior component has a superior component top side and a superior component bottom side. The superior component is configured to be received in the intervertebral space whereby the superior component top side abuts against the first vertebra. The inferior component has an inferior component top side and an inferior component bottom side. The inferior component is configured to be received in the intervertebral space whereby the inferior component bottom side abuts against the second vertebra. The superior component bottom side and the inferior component top side oppose each other when the superior and inferior components are received in the intervertebral space.

The superior and inferior components inter-engage with each other whereby: at least a part of one of the superior and inferior components is constrained to move in an anterior-posterior direction relative to the other of the superior and inferior components; and resistance is presented to movement of the at least a part of one of the superior and inferior components relative to the other of the superior and inferior components in each of a direction of separation of the superior and inferior components and a direction, i.e. a transverse direction, orthogonal to the anterior-posterior direction and to the direction of separation. The at least a part of one of the superior and inferior components may comprise a respective one of at least a part of the superior component top side and at least a part of the inferior component bottom side.

Each of the at least a part of one of the superior and inferior components and the other of the superior and inferior components is configured to engage with its respective vertebra whereby force is coupled between it and its respective vertebra. Each of the at least a part of one of the superior and inferior components and the other of the superior and inferior components may be configured to inter-engage with its respective vertebra. Each of the at least a part of one of the superior and inferior components and the other of the superior and inferior components may be configured to engage by being shaped to abut against an aspect of the respective vertebra facing in the anterior-posterior direction.

Each of the at least a part of one of the superior and inferior components and the other of the superior and inferior components may be configured by way of teeth protruding from it. The teeth may inter-engage with the respective vertebra whereby force applied to the component is coupled to the vertebra and vice-versa.

Alternatively or in addition, each of the at least a part of one of the superior and inferior components and the other of the superior and inferior components may define at its anterior end at least one aperture for receiving a fixing member for fixing to a respective one of the first and second vertebrae. On reception of the superior and inferior components in the intervertebral space, each of the at least a part of one of the superior and inferior components and the other of the superior and inferior components is fixed to its respective one of the first and second vertebrae.

Constrained movement in the anterior-posterior direction of the at least a part of one of the superior and inferior components and the other of the superior and inferior components relative to each other enable the at least a part of one of the superior and inferior components and the other of the superior and inferior components to be misaligned with each other in the anterior-posterior direction to reflect the spondylolisthesis to be corrected.

The locking mechanism allows for movement of the at least a part of one of the superior and inferior components in the anterior-posterior direction that increases an extent of overlap of the at least a part of one of the superior and inferior components and the other of the superior and inferior components, i.e. a first anterior-posterior direction. Increase in the extent of overlap may decrease an extent of spondylolisthesis and may be achieved by the surgeon's action to decrease the extent of spondylolisthesis. Furthermore, the locking mechanism presents resistance to movement of the at least a part of one of the superior and inferior components in the anterior-posterior direction that decreases an extent of overlap of the at least a part of one of the superior and inferior components and the other of the superior and inferior components, i.e. a second anterior-posterior direction opposite the first anterior-posterior direction. The locking mechanism may thus present resistance to a decrease in extent of overlap and hence increase in extent of spondylolisthesis, such as when there is a pause in the surgeon taking action to decrease the extent of spondylolisthesis.

The superior component may abut against the first vertebra only of the first and second vertebrae. The inferior component may abut against the second vertebra only of the first and second vertebrae.

Spondylolisthesis usually involves the first vertebra, i.e. the upper vertebra, being displaced in the anterior direction relative to the second vertebra, i.e. the lower vertebra. Therefore, inter-engagement between superior and inferior components may be such that at least a part of the superior component is constrained to move in an anterior-posterior direction relative to the inferior component. In addition, inter-engagement between superior and inferior components may be such that resistance is presented to movement of the at least a part of the superior component relative to the inferior component in each of a direction of separation of the superior and inferior components and a direction orthogonal to the anterior-posterior direction and to the direction of separation. Furthermore, the locking mechanism may allow for movement of the at least a part of the superior component in the anterior-posterior direction which increases an extent of overlap of the at least a part of the superior component and the inferior component and presents resistance to movement of the at least a part of the superior component in the anterior-posterior direction which decreases an extent of overlap of the at least a part of the superior component and the inferior component.

The at least a part of one of the superior and inferior components may be shaped at its anterior end to abut against an anterior aspect of the respective one of the first and second vertebrae. Alternatively or in addition, the other of the superior and inferior components may be shaped at its anterior end to abut against an anterior aspect of the respective one of the first and second vertebrae. The component may be shaped by comprising a lug which extends from an anterior end of a main part of the component, the lug being at an angle to the main part of the component. The lug may abut against the anterior aspect of the respective vertebra when the component is received in the intervertebral space whereby force may be exerted against the vertebra to correct spondylolisthesis. The at least one aperture may be defined in the lug.

According to a first embodiment of the anterior lumbar interbody fusion device, the superior and inferior components may inter-engage with each other whereby: the superior and inferior components are constrained to move in an anterior-posterior direction relative to each other; and resistance is presented to movement of the superior and inferior components relative to each other in each of a direction of separation of the superior and inferior components and a direction orthogonal to the anterior-posterior direction and to the direction of separation. Likewise, each of the superior and inferior components may be configured to engage with its respective vertebra whereby force is coupled between it and its respective vertebra. More specifically, each of the superior and inferior components may define at its anterior end the at least one aperture for receiving a fixing member for fixing to a respective one of the first and second vertebrae. Also, the locking mechanism may allow for relative movement of the superior and inferior components in the anterior-posterior direction which increases an extent of overlap of the superior and inferior components and may present resistance to relative movement of the superior and inferior components in the anterior-posterior direction which decreases an extent of overlap of the superior and inferior components. The superior and inferior components may thus move relative to each other rather than a part of one of the superior and inferior components moving relative to the other of the superior and inferior components.

The superior and inferior components may inter-engage directly with each other, i.e. without an intervening component. Furthermore, each of the superior and inferior components may be unitary and more specifically may be integrally formed.

The superior component may define a superior component profile and the inferior component may define an inferior component profile, the superior and inferior component profiles inter-engaging with each other. More specifically, the superior and inferior component profiles may be configured for linear translation of one profile in relation to the other to thereby provide for movement in the anterior-posterior direction. Furthermore, the superior and inferior component profiles may be configured to restrict, and more specifically substantially prevent, relative movement of the superior and inferior components in a transverse direction. In addition, the superior and inferior component profiles may be configured to restrict, and more specifically substantially prevent more than limited, relative movement of the superior and inferior components in a direction of separation of the superior and inferior components, i.e. in a direction of separation of the first and second vertebrae.

One of the superior and inferior component profiles may define a channel which extends in the anterior-posterior direction and the other of the superior and inferior component profiles may define a formation which is received in and travels along the channel. More specifically, the inferior component profile may define the channel.

In a first form, the formation defined by the other of the superior and inferior component profiles may have the form of a protrusion, such as a cylindrical protrusion, which extends in the transverse direction. The protrusion may travel along the channel to change an extent of overlap of the superior and inferior components. Furthermore, the superior and inferior components may be configured such that the protrusion is rotatable in the channel whereby an inclination of the superior and inferior components to each other may be changed. More specifically, the protrusion may be disposed towards a posterior end of the other of the superior and inferior component profiles to thereby present a barrier to movement apart of the superior and inferior components towards their posterior ends whilst allowing for moving apart of the superior and inferior components at their anterior ends by virtue of rotation. As described further below, such a configuration may allow for use of a core component to determine angulation of the superior and inferior components to each other.

In a second form, the formation defined by the other of the superior and inferior component profiles may have the form of an elongate protrusion which extends in the anterior-posterior direction. The elongate protrusion may be slidably received in the channel to provide for change in extent of overlap of the superior and inferior components whilst presenting a barrier to separation of the superior and inferior components.

In each of the first and second forms, the superior component may define first and second superior component profiles which are spaced apart in the transverse direction and the inferior component may define first and second inferior component profiles which are spaced apart in the transverse direction. The first superior component profile and the first inferior component profile may inter-engage with each other and the second superior component profile and the second inferior component profile may inter-engage with each other to thereby present resistance and more specifically a barrier to relative movement of the superior and inferior components in the transverse direction.

The first and second superior component profiles may be towards a respective transverse side of the superior component and the first and second inferior component profiles may be towards a respective transverse side of the inferior component.

Each of the first and second inferior component profiles may respectively define first and second channels, the first and second channels facing each other. Furthermore, each of the first and second superior component profiles may respectively define first and second formations, the first formation being slidably received in the first channel and the second formation being slidably received in the second channel.

In an embodiment, the anterior lumbar interbody fusion device may lack the core component described below. In this embodiment, there may be no component, such as a core component, between the superior and inferior components.

Furthermore, according to this embodiment the superior component top side and the superior component bottom side may lie in substantially parallel planes and the inferior component bottom side and the inferior component top side may lie in substantially parallel planes whereby there is substantially no inclination between the superior and inferior components when they are installed in the intervertebral space.

Alternatively according to this embodiment, at least one of: the superior component top side and the superior component bottom side may be inclined to each other; and the inferior component bottom side and the inferior component top side may be inclined to each other. At least one of the superior and inferior components may therefore have the form of a wedge. Furthermore, an upper side and a lower side of the component may not meet at an acute angle whereby the component has the form of a frustum of a wedge. Furthermore, the inclination may be such that the component is thicker towards the anterior side than towards the posterior side. In a form, only the superior component of the superior and inferior components may have the form of a wedge.

In a different embodiment, the anterior lumbar interbody fusion device may comprise a core component configured for insertion between the superior and inferior components whereby a separation between the superior and inferior components is determined when the anterior lumbar interbody fusion device is in the intervertebral space.

An upper side and a lower side of the core component may be inclined to each other. The core component may therefore have the form of a wedge. Furthermore, the upper side and a lower side may not meet at an acute angle whereby the core component has the form of a frustum of a wedge. An inclination of the inferior and superior components relative to each other may thus be determined by way of the core component further to a separation between the inferior and superior components. Extent of inclination of the inferior and superior components may be determined by selection from a plurality of core components having upper and lower sides of different inclinations. Such selection may be combined with selection from a plurality of core components having different heights.

Where the superior and inferior components do not inter-engage directly with each other, the core component may provide for inter-engagement between the superior and inferior components. The core component may therefore inter-engage with each of the superior and inferior components whereby the superior and inferior components inter-engage with each other.

Irrespective of whether or not the superior and inferior components inter-engage directly with each other, the superior component and the core component may be configured to inter-engage with each other to present resistance and more specifically substantially prevent movement apart of the superior component and the core component. Alternatively or in addition, the superior component and the core component may be configured to inter-engage with each other to present resistance and more specifically substantially prevent relative movement of the superior component and the core component in the transverse direction.

The superior and core components may define surface profiles which cooperate to provide inter-engagement of the superior and core components which presents resistance and more specifically substantially prevents movement apart of the superior and core components. In addition, the surface profiles may provide for sliding engagement of the superior and core components when the core component is moved in the anterior-posterior direction relative to the superior component and more specifically such that resistance and more specifically a barrier is presented to relative movement of the superior and core components in the transverse direction. The superior and core components may be brought first into sliding engagement to progressively increase an extent of overlap of the superior and core components.

The cooperating surface profiles may be shaped such that inter-engagement involving presenting resistance to movement apart of the superior and core components occurs when the superior and core components are at least one of: substantially half overlapping; and nearing full overlap.

The cooperating surface profiles may be shaped to draw the superior and core components together. More specifically the cooperating surface profiles may define surfaces which are inclined to a plane in which the anterior-posterior direction and the transverse direction lie and which ride over each other as the core component moves in the posterior direction relative to the superior component.

The superior component may define at least one surface profile, and more specifically two surface profiles spaced apart in the transverse direction, towards each of a posterior end of the superior component and an anterior end of the superior component and the core component may define at least one surface profile, and more specifically two surface profiles spaced apart in the transverse direction, towards each of a posterior end of the core component and an anterior end of the core component. The profiles at the posterior ends of the superior and core components may cooperate with each other and the profiles at the anterior ends of the superior and core components may cooperate with each other.

The cooperating surface profiles may be shaped such that upon movement of the core component in the posterior direction the cooperating surface profiles abut whereby the superior component moves in the posterior direction with the core component. When the core and superior components are substantially fully overlapping, and perhaps also when the core and superior components are locked together by way of the second locking mechanism described below, the core and superior components may be moved together relative to the inferior component to reduce an extent of spondylolisthesis.

The anterior lumbar interbody fusion device may comprise a second locking mechanism which is operative to present resistance and more specifically a barrier to relative movement of the core and superior components in the anterior-posterior direction which decreases an extent of overlap of the core and superior components. More specifically, the second locking mechanism may be operative to present resistance only when the core and superior components are substantially fully overlapping. Therefore, the second locking mechanism may be disengaged before the core and superior components are substantially fully overlapping whereby relative movement of the core and superior components is not resisted and may be engaged when the core and superior components are substantially fully overlapping. The second locking mechanism may comprise a second locking mechanism first part comprised in and more specifically integrally formed with the core component and a second locking mechanism second part comprised in and more specifically integrally formed with the superior component.

The second locking mechanism may be brought into engagement by relative movement of the core and superior components and more specifically relative movement in the anterior-posterior direction. Relative movement in the anterior-posterior direction may be provided by slidable engagement between the core and superior components. Slidable engagement between the core and superior components may be provided by the surface profiles of the core and superior components, as described above.

One of the second locking mechanism first and second parts may comprise a first profile defined by the respective one of the core and superior components and the other of the second locking mechanism first and second parts may comprise a second profile movably mounted on the respective one of the core and superior components. The second profile may move to a position in which the second profile engages with the first profile.

One of the second locking mechanism first and second parts may comprise two first profiles which are spaced apart from each other in the transverse direction. Also, the other of the second locking mechanism first and second parts may comprise two second profiles which are spaced apart from each other in the transverse direction. The two first profiles and the two second profiles may be disposed in their respective components such that each of the two first profiles engages with a respective one of the two second profiles.

The first profile may be a recess. More specifically, the recess may be defined by the core component. The second profile may be a protrusion shaped to be received in the recess. More specifically, the protrusion may be comprised in the superior component. The second locking mechanism may be engaged when the second profile is received in the recess.

Where the second profile is a protrusion, the protrusion may extend from a sprung portion which urges the protrusion in an inter-engaging direction towards the recess. The sprung portion may be a cantilever spring with, more specifically, the protrusion extending from towards a distal end of the cantilever spring. The sprung portion may be straight or tapered. Tapering controls stiffness and hence extent of deflection. A cantilever sprung structure may be simpler and more compact than other means of providing spring bias. A more compact structure is desirable in an anterior lumbar interbody fusion device in which space is usually at a premium. The cantilever sprung structure may lie along the anterior-posterior direction whereby little space is occupied by the cantilever sprung structure in the transverse direction.

Where there are two second profiles in the form of a protrusion, each of the two protrusions may extend from a respective one of two sprung portions. The two protrusions may extend in opposite directions. Alternatively or in addition, the two sprung portions may be spaced apart from each other in the transverse direction. Furthermore, the two sprung portions may be located towards a line which bisects the respective one of the core and superior components and more specifically towards a bisecting line which extends in the anterior-posterior direction.

The locking mechanism, i.e. first locking mechanism rather than the second locking mechanism described immediately above, allows for movement of the at least a part of one of the superior and inferior components in the anterior-posterior direction which increases an extent of overlap of the at least a part of one of the superior and inferior components and the other of the superior and inferior components and presents resistance to movement of the at least a part of one of the superior and inferior components in the anterior-posterior direction which decreases an extent of overlap of the at least a part of one of the superior and inferior components and the other of the superior and inferior components.

More specifically, the first locking mechanism allows for movement of at least a part of the superior component in the anterior-posterior direction which increases an extent of overlap of the at least a part of the superior component and the inferior component and presents resistance to movement of the at least a part of the superior component in the anterior-posterior direction which decreases an extent of overlap of the at least a part of the superior component and the inferior component.

In a first embodiment of the first locking mechanism, the first locking mechanism may be of a form and function as described above for the second locking mechanism. For example, and in respect of finer features, the second locking mechanism may comprise: two transversely spaced apart cantilever springs on the core component or superior component with a protrusion extending from towards a distal end of each cantilever spring; and two transversely spaced apart recesses on the inferior component, each protrusion being received in a respective one of the two recesses when the first locking mechanism is engaged.

According to the first embodiment of the first locking mechanism, and where the anterior lumbar interbody fusion device comprises a core component, the core and superior components may be coupled together, such as by way of the second locking mechanism described above, whereby the core and superior components move together in the anterior-posterior direction relative to the inferior component. The two transversely spaced apart cantilever springs may therefore be on the core component whereby the superior component moves with the core component. Alternatively, and where the anterior lumbar interbody fusion device lacks a core component, the two transversely spaced apart cantilever springs may be on the superior component. The first locking mechanism may thus involve inter-engagement directly between the superior and inferior components.

As described above, correction of spondylolisthesis may involve the surgeon moving one vertebra progressively or perhaps even stage-by-stage in the anterior-posterior direction relative to the adjacent vertebra. It may therefore be advantageous for the anterior lumbar interbody fusion device to resist decrease in overlap of the superior and inferior components at each of plural different extents of overlap. For example, the surgeon may first increase overlap and hence reduce spondylolisthesis to an initial extent before pausing to further increase overlap and hence further reduce spondylolisthesis. To address this, the first locking mechanism may be configured to present resistance to movement of the at least a part of the superior component in the anterior-posterior direction which decreases an extent of overlap of the at least a part of the superior component and the inferior component at each of plural different extents of overlap.

A first profile of the first locking mechanism may define plural locking formations, and more specifically recesses, which are spaced apart along the anterior-posterior direction. A second profile of the first locking mechanism may be movably mounted on its respective component to engage with each of the plural locking formations. Furthermore, the plural locking formations and the second profile may have the form of a ratchet whereby movement in the posterior direction is allowed and movement in the anterior direction is resisted. As mentioned above, the first locking mechanism may be of a form and function as described above for the second locking mechanism. The first locking mechanism may therefore comprise one or more further features of the second locking mechanism apart from the plural locking formations.

In a second embodiment of the first locking mechanism, the first locking mechanism may comprise a driving member which engages with each of the core component and the inferior component, the driving member being user operable to urge the core component over the inferior component and to thereby increase an extent of overlap of the core and inferior components. In this embodiment, the anterior lumbar interbody fusion device comprises a core component along with the superior and inferior components.

The first locking mechanism of the second embodiment may further comprise a threaded profile, and more specifically a threaded bore, comprised in one of the core component and the inferior component, and more specifically comprised in the inferior component, and an aperture defined by the other of the core component and the inferior component, and more specifically defined by the core component. Furthermore, the driving member may be configured to be received through the aperture for threaded engagement with the threaded profile, a driving member profile, such as a shoulder, of the driving member abutting against a periphery of the aperture. Rotation of the driving member, such as by a surgeon, may cause the driving member to move along the threaded profile in the posterior direction while abutting against the periphery of the aperture to thereby urge the core component and inferior component together and increase their extent of overlap.

According to a second embodiment of the anterior lumbar interbody fusion device, one of the superior and inferior components may comprise first and second component parts, the first component part moving relative to the other of the superior and inferior components in the anterior-posterior direction to change an extent of overlap between the first component part and the other of the superior and inferior components. Furthermore, the first component part may move relative to the second component part whereby there is substantially no change in extent of overlap between the second component part and the other of the superior and inferior components.

The first and second component parts may be comprised in the superior component.

The first component part and the second component part may define cooperating profiles which allow for relative movement of the first and second component parts. One of the first and second component parts, and more specifically the second component part, may define a channel in which part of the other of the first and second component parts is slidably received. More specifically, one of the first and second component parts may define two channels which are spaced apart in the transverse direction and which oppose each other. Furthermore, the other of the first and second component parts may define first and second edges at opposite transverse sides which are each shaped to be slidably received in a respective one of the two channels.

The first and second component parts may engage with each other such that the first component part is adjacent and can therefore abut against a vertebra. For example, and where the first and second component parts are comprised in the superior component, the first component part may be on a side of the second component part oppositely directed to the inferior component bottom side.

The second embodiment of the anterior lumbar interbody fusion device may further comprise a core component. The first component part and the core component may be configured to mechanically couple with each other whereby movement of the core component is coupled to the first component part to cause movement of the first component relative to the second component part. Movement of the core component, such as by a surgeon, may move the first component part relative to the second component part whereby extent of overlap is changed.

The first component part and the core component may be configured to mechanically couple with each other by way of cooperating formations. The core component may define a first formation, such as a formation surface, and the first component part may define a second formation, such as a formation protrusion, the formation protrusion and formation surface being shaped and located such that the formation protrusion bears against the formation surface to thereby mechanically couple movement of the core component to the first component part.

As described above, the second component part may be between the first component part and the core component. The second component part may therefore define an elongate aperture through which the formation protrusion extends and along which the formation protrusion travels.

The first component part and the core component may be configured to mechanically couple with each other by way of two pairs of cooperating formations, the two pairs of cooperating formations being spaced apart from each other in the transverse direction.

The superior and inferior components may be mechanically coupled to each other to restrict their relative movement in the transverse direction and in the anterior-posterior direction. More specifically, the superior and inferior components may be mechanically coupled for their relative rotation, such as by way of a hinge, about a rotation axis towards the posterior end. The inclination of the superior and inferior components to each other may thus be changed to receive differently angled core components.

The superior and inferior components may be mechanically coupled for their relative rotation and for relative movement in the direction of spacing apart of the superior and inferior components, i.e. in a translation direction which is orthogonal to each of the anterior-posterior direction and the transverse direction. More specifically, the superior and inferior components may be mechanically coupled by a hinge pin received in an elongate recess which extends in the translation direction.

The locking mechanism for the second embodiment of the anterior lumbar interbody fusion device may be of the same shape and form as described above in respect of the second embodiment of first locking mechanism except as will now be described. The threaded profile may be comprised in the second component part of the superior component and the aperture may be defined by the core component. The driving member may therefore move along the threaded profile whilst bearing against and thereby moving the core component, with movement of the core component being coupled to the first component part. Otherwise, the locking mechanism for the second embodiment of the anterior lumbar interbody fusion device may comprise one or more features of the first locking mechanism.

The anterior lumbar interbody fusion device may have dimensions appropriate for use as such. The superior component may have a range of length by width from 20 mm by 20 mm to 50 mm by 50 mm. The superior component may have a range of height at the posterior end from 1 mm to 4 mm. The inferior component may have a range of length by width from 20 mm by 20 mm to 50 mm by 50 mm. The inferior component may have a range of height at the posterior end from 1 mm to 4 mm. The core component may have a range of length by width from 20 mm by 20 mm to 50 mm by 50 mm. The core component may have a range of height at the posterior end from 4 mm to 10 mm.

Each of the superior and inferior components may have the form of a plate, albeit a plate having structures thereon that provide for inter-engagement as described above, whereby each is thin relative to its length and width. At least one of the superior component top side and the inferior component bottom side may be shaped in the coronal or sagittal planes, for example domed, to enhance fit and contact with adjacent vertebrae.

At least one of the superior and inferior components and the core component may have at least one aperture extending therethrough in a direction of separation of the inferior and superior components. Such at least one aperture may provide for distribution of bone graft material and, more specifically, where the at least one aperture is in the superior or inferior component, the at least one aperture may allow passage for bone graft material to engage with the adjacent vertebra.

At least one of the core component, the superior component and the inferior component may be formed by the like of casting, moulding or printing. Alternatively, at least one of the core component, the superior component and the inferior component may be formed by the like of machining or stamping.

At least one of the superior component, the core component and the inferior component may be formed from a metal, such as titanium, or a metal alloy, such as stainless steel, Ti6Al4V, CoCr or nitinol. Nitinol may be useful in respect of cooperating parts of the superior component, the core component and the inferior component. At least one of the superior component, the core component and the inferior component may be formed from a plastics material and more specifically a thermoplastic polymer, such as PEEK, carbon reinforced PEEK or UHMWPE (Ultra High Molecular Weight PolyEthylene). In forms of the invention, the core component may be formed by 3D printing whereby the core component has the form of a 3D lattice. The aforementioned materials may be used to form the core component by way of 3D printing.

References herein to anterior or to anterior aspect are in respect of the patient. Thus, the anterior side or aspect is the front of the patient. Correspondingly, references herein to posterior or to posterior aspect are in respect of the patient. Thus, the posterior side or aspect is the back of the patient. The anterior and posterior aspects are therefore oppositely directed.

According to a second aspect of the present invention there is provided a method of correcting spondylolisthesis with an anterior lumbar interbody fusion device, the anterior lumbar interbody fusion device being receivable in an intervertebral space between first and second vertebrae and comprising a superior component, an inferior component and a locking mechanism, the method comprising:
  receiving the superior component in the intervertebral space, the superior component having a superior component top side and a superior component bottom side, the superior component top side abutting against the first vertebra;
  receiving the inferior component in the intervertebral space, the inferior component having an inferior component top side and an inferior component bottom side, the inferior component bottom side abutting against the second vertebra, the superior component bottom side and the inferior component top side opposing each other when the superior and inferior components are received in the intervertebral space;
  bringing the superior and inferior components into inter-engagement with each other whereby: at least a part of one of the superior and inferior components is constrained to move in an anterior-posterior direction relative to the other of the superior and inferior components; and resistance is presented to movement of the at least a part of one of the superior and inferior components relative to the other of the superior and inferior components in each of a direction of separation of the superior and inferior components and a direction orthogonal to the anterior-posterior direction and to the direction of separation, each of the at least a part of one of the superior and inferior components and the other of the superior and inferior components is configured to engage with its respective vertebra whereby force is coupled between it and its respective vertebra; and
  moving the at least a part of one of the superior and inferior components in the anterior-posterior direction which increases an extent of overlap of the at least a part of one of the superior and inferior components and the other of the superior and inferior components, the locking mechanism allowing said extent of overlap increasing movement but presenting resistance to movement of the at least a part of one of the superior and inferior components in the anterior-posterior direction which decreases an extent of overlap of the at least a part of one of the superior and inferior components and the other of the superior and inferior components.

Embodiments of the second aspect of the present invention may comprise one or more features of the first aspect of the present invention.

BRIEF DESCRIPTION OF DRAWINGS

Further features and advantages of the present invention will become apparent from the following specific description, which is given by way of example only and with reference to the accompanying drawings, in which:

FIG. 2A is a perspective view from a corner and below of a superior component of a second embodiment of anterior lumbar interbody fusion device;

FIG. 2B is a perspective view from above of the superior component of FIG. 2A;

FIG. 2C is a view from below of the superior component of FIG. 2A;

FIG. 2D is a perspective view from above of an inferior component of the second embodiment of anterior lumbar interbody fusion device;

FIG. 2E is a perspective view from below of the inferior component of FIG. 2D;

DESCRIPTION OF EMBODIMENTS

Figure 1A:
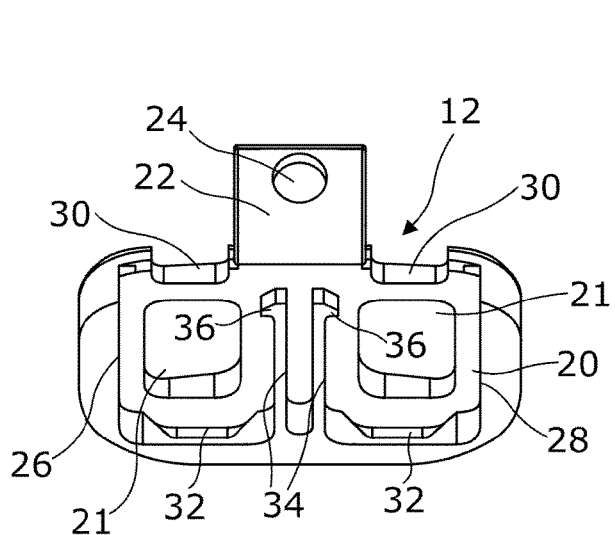
FIG. 1A is a perspective view from below of a superior component of a first embodiment of anterior lumbar interbody fusion device.
Figure 1B:
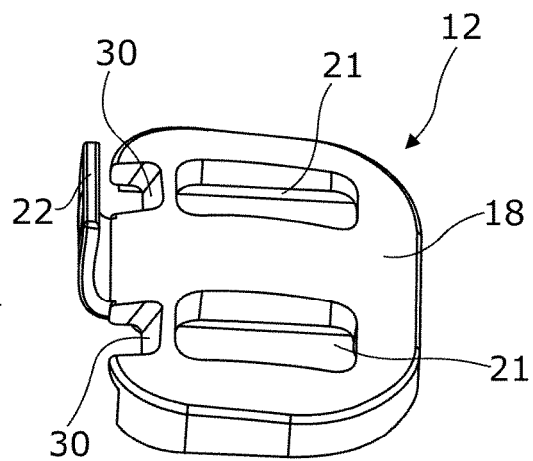
FIG. 1B is a perspective view from above of the superior component of FIG. 1A.
Figure 1C:
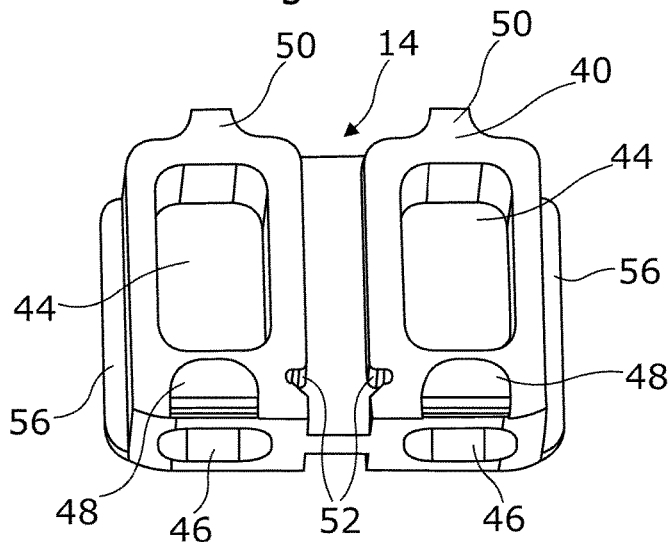
FIG. 1C is a view from above of a core component of the first embodiment of anterior lumbar interbody fusion device.
Figure 1D:
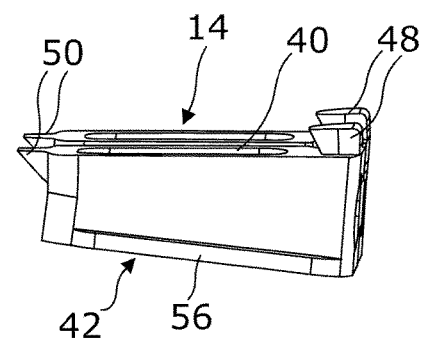
FIG. 1D is a view from a side of the core component of FIG. 1C.
Figure 1E:
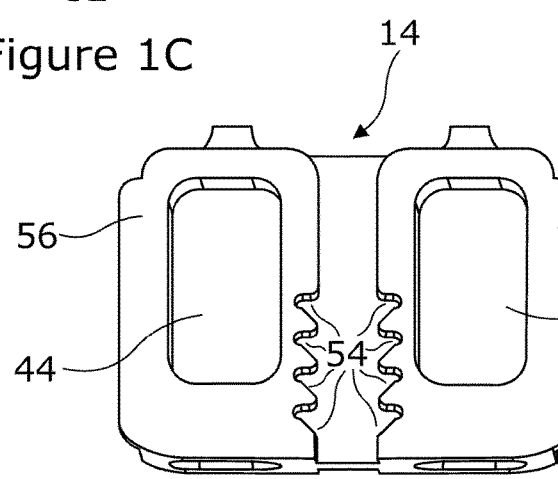
FIG. 1E is a view from below of the core component of FIG. 1C.
Figure 1F:
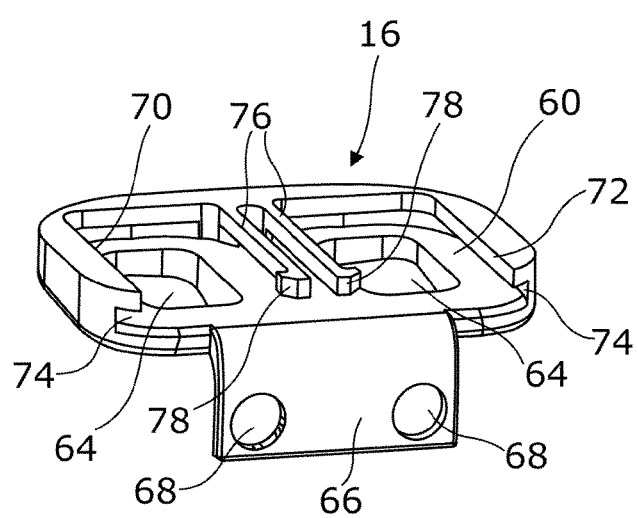
FIG. 1F is a perspective view from above of an inferior component of the first embodiment of anterior lumbar interbody fusion device.
Figure 1G:
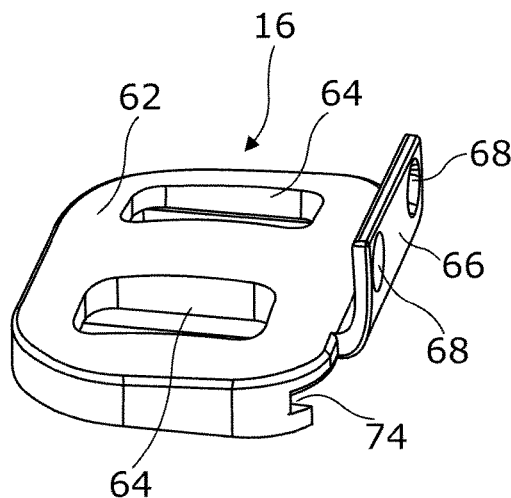
FIG. 1G is a perspective view from below of the inferior component of FIG. 1F.
Figure 1H:
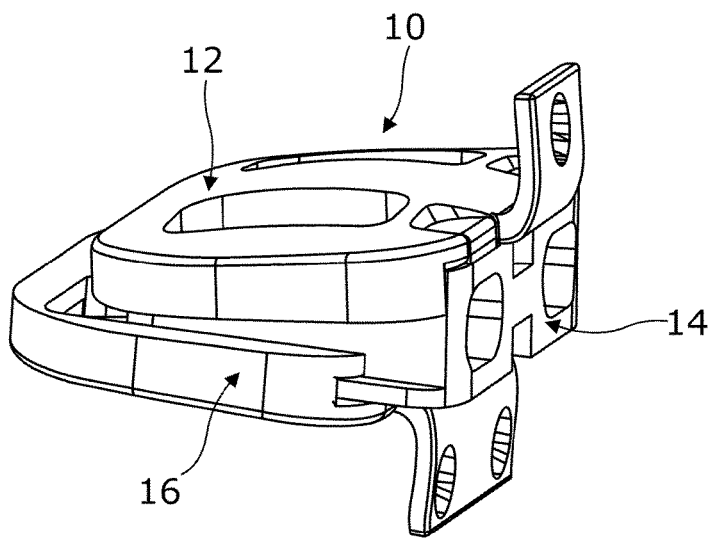
FIG. 1H is a perspective view from above of the first embodiment of anterior lumbar interbody fusion device when assembled and before correction of spondylolisthesis.
Figure 1I:
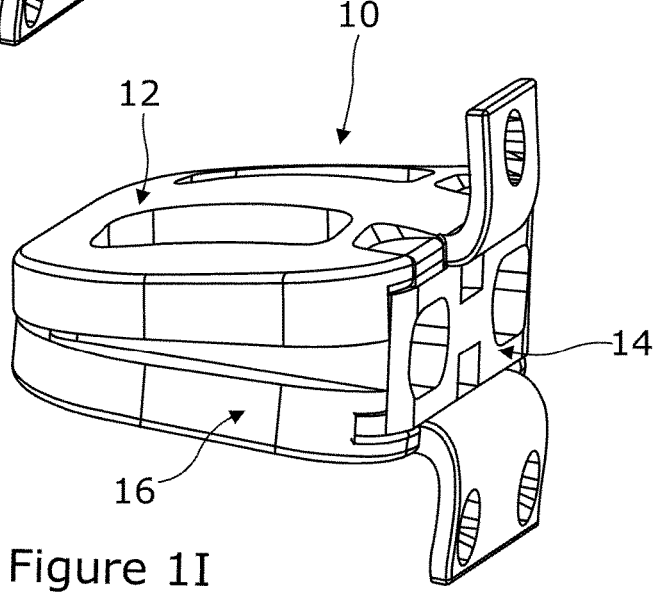
FIG. 1I is a perspective view from above of the first embodiment of anterior lumbar interbody fusion device when assembled and after correction of spondylolisthesis.

A first embodiment of anterior lumbar interbody fusion device 10 is shown in FIGS. 1A to 1I. An anterior lumbar interbody fusion (ALIF) device is introduced into a patient's intervertebral space between first and second adjacent vertebrae from the anterior side of the patient. The first embodiment of anterior lumbar interbody fusion device 10 comprises a superior component 12, a core component 14 and an inferior component 16. Perspective views of the superior component 12 from below and above are shown respectively in FIGS. 1A and 1B. Views of the core component 14 from above, one side and below are shown respectively in FIGS. 1C to 1E. Perspective views of the inferior component 16 from above and below are shown respectively in FIGS. 1F and 1G. FIG. 1H is a perspective view from above of the first embodiment of anterior lumbar interbody fusion device 10 when assembled and installed in an intervertebral space of a patient and before correction of spondylolisthesis. FIG. 1H shows the anterior lumbar interbody fusion device 10 before correction of a Grade 2 spondylolisthesis. FIG. 1I is a perspective view from above of the first embodiment of anterior lumbar interbody fusion device 10 when assembled and after correction of the spondylolisthesis.

Each of the superior component 12 and the inferior component 16 is generally of the form of a plate, albeit a plate having structures thereon and two spaced apart apertures therethrough. The core component 14 has the form of a frustum of a wedge. The anterior lumbar interbody fusion device 10 is assembled and installed in the intervertebral space first by insertion of the superior component 12 and the inferior component 16 into the intervertebral space with an insertion tool of known form and function. The insertion tool also holds the superior component 12 and the inferior component 16 within the intervertebral space. For example, a Prodisc® L inserter from Centinel Spine, Inc., 900 Airport Road, Suite 3A, West Chester, Pa. 19380, USA is used as the insertion tool after modification to take account of the offset of the vertebrae. The inserted superior and inferior components are fixed with screws to the lower or second vertebra. Alternatively, screw fixing of at least one of the inserted superior and inferior components and more typically of the superior component is deferred until after insertion of the core component between the superior and inferior components and correction of the spondylolisthesis. The insertion tool is then used to insert the core component 14 between the superior and inferior components 12, 16. On account of the offset of the superior and inferior components 12, 16 caused by the spondylolisthesis, the core component 14 inter-engages in the intervertebral space first with the superior component. Upon further insertion, the core component begins to slidably inter-engage with the inferior component. Following further insertion of the core and when the superior and core components 12, 14 are fully inter-engaged with each other they are then moved together in the posterior direction relative to the inferior component 16 such that the extent of overlap of the superior and inferior components 12, 16 increases until the superior component 12 is aligned with the upper or first vertebra. As mentioned above, the superior component 12 is fixed with a screw to the upper vertebra either during the procedure or upon conclusion of the procedure. At this stage in the procedure, the anterior lumbar interbody fusion device 10 has the disposition shown in FIG. 1H which reflects the extent of spondylolisthesis before correction. The surgeon then manipulates the patient to correct the spondylolisthesis with this involving further movement of the superior and core components 12, 14 together in the posterior direction relative to the inferior component 16 to increase the extent of overlap of the superior and inferior components until the spondylolisthesis is corrected. At this stage in the procedure, the anterior lumbar interbody fusion device 10 has the disposition shown in FIG. 1I. As will become clear from the following description, the anterior lumbar interbody fusion device 10 is configured to resist spondylolisthesis increasing movement of the superior and core components 12, 14 together in the anterior direction. Further description is provided below of form and function in respect of the like of inter-engagement of the superior and core components 12, 14, inter-engagement of the core and inferior components 14, 16, fixing of the superior and inferior components 12, 16 to vertebrae, and resistance to spondylolisthesis increasing movement of the superior and core components 12, 14 together in the anterior direction.

Turning now to FIGS. 1A and 1B, the superior component 12 is integrally formed from a metal or plastics material and has a superior component top side 18 and a superior component bottom side 20. The superior component 12 is of a size such that it can be received in the intervertebral space whereby the superior component top side 18 abuts against the upper vertebra. The superior component 12 defines two apertures 21 which extend therethrough and are spaced apart from each other in the transverse direction. The two apertures 21 allow for passage of bone graft material from inside the anterior lumbar interbody fusion device 10. The superior component 12 has an integrally formed superior lug 22 which extends from an anterior end of the superior component and substantially orthogonally to the superior component top side 18 such that the superior lug extends above the superior component top side. The superior lug 22 defines a superior lug aperture 24 extending therethrough. As described above, the surgeon aligns the superior component 12 with the upper vertebra and fixes the superior component 12 with a screw to the upper vertebra. Considering this latter part of the surgical procedure further, the superior component 12 is aligned with the upper vertebra by moving the superior component 12 together with the core component 14 in the posterior direction into the intervertebral space until the superior lug 22 abuts against the anterior aspect of the upper vertebra. The surgeon then drives the screw through the superior lug aperture 24 and into the upper vertebra to fix the superior component 12 to the upper vertebra. Alternatively, screw fixing is deferred until the spondylolisthesis has been corrected.

Considering FIG. 1A in particular, the superior component 12 defines integrally formed structures at the superior component bottom side 20. The structures comprise first and second straight walls 26, 28 which each extend up from the superior component bottom side 20 and away from the superior component top side 18. Each of the first and second walls 26, 28 is towards a respective transverse side of the superior component 12 such that the first and second walls are parallel and face each other. The first and second walls 26, 28 run in the anterior-posterior direction. As described further below, the first and second walls engage with sides of the core component 14 and guide movement of the core component relative to the superior component 12 as the core component is being brought into inter-engagement with the superior component.

The structures at the superior component bottom side 20 further comprise first and second anterior recesses 30 and first and second posterior recesses 32. The first and second anterior recesses 30 are defined in the anterior edge of the superior component 12 and such that they are spaced apart from each other in the transverse direction. As can be seen from FIG. 1B, the base of each of the first and second anterior recesses 30 is inclined to a plane in which the anterior-posterior direction and the transverse direction lie whereby the base of the recess slopes upwards away from the anterior side. As described further below, a sloped surface of a corresponding protrusion on the core component 14 rides over the sloped base of each anterior recess 30 to draw the core component and superior component together and into inter-engagement. The first and second posterior recesses 32 are defined in a respective one of aligned posterior walls near the posterior side of the superior component 12. The posterior walls extend in the transverse direction and up from the superior component bottom side 20. The first and second posterior recesses 32 are therefore spaced apart from each other in the transverse direction. Each of the first and second posterior recesses 32 is elongate in the transverse direction and extends in the orthogonal direction up from the base of its posterior wall. Each of the first and second posterior recesses 32 is inclined to a plane in which the anterior-posterior direction and the transverse direction lie whereby the posterior recess is sloped between its leading edge and its base. As described further below, a sloped surface of a corresponding protrusion on the core component 14 rides over the sloped posterior recess 32 to draw the core component and superior component together and into inter-engagement.

The structures at the superior component bottom side 20 further comprise first and second superior cantilever spring structures 34. Each cantilever spring structure 34 comprises a cantilever spring member which extends at its proximal end from near the posterior end of the superior component 12 to near the anterior end of the superior component. A protrusion 36 extends in the transverse direction from towards a distal end of the cantilever spring member. The two cantilever spring members are substantially parallel and each of the cantilever spring members is substantially parallel with and facing a respective one of the first and second straight walls 26, 28. The first and second superior cantilever spring structures 34 are located on a respective side of a line which bisects the superior component 12 and which extends in the anterior-posterior direction whereby the first and second superior cantilever spring structures are spaced apart to a small extent from each other in the transverse direction. Furthermore, the protrusions 36 project in opposite directions from their respective cantilever spring members towards their respective first and second straight walls 26, 28. As described further below, each of the protrusions 36 on the first and second superior cantilever spring structures 34 is received in a respective recess defined by the core component 14 to lock the superior component 12 and the core component together. The first and second superior cantilever spring structures 34 and the recesses on the core component constitute a second locking mechanism.

Turning now to FIGS. 1C to 1E, the core component 14 is integrally formed from a metal or plastics material and has an upper side 40 and a lower side 42. As can be seen from FIG. 1D, the upper side 40 and the lower side 42 are inclined to each other and do not meet at an acute angle whereby the core component 14 has the form of a frustum of a wedge with the thickest part of the wedge at the anterior side of the core component. The core component defines two bone graft material receiving spaces 44 which are spaced apart from each other in the transverse direction with each bone graft material receiving space extending from the upper side 40 to the lower side 42. Two spaced apart bone graft material receiving apertures 46 are defined in the anterior side of the core component 14 such that they are spaced apart from each other in the transverse direction. Each bone graft material receiving aperture 46 is in fluid communication with a respective one of the two bone graft material receiving spaces 44 whereby bone graft material can be introduced into the receiving space 44 by way of the bone graft material receiving aperture. When the superior component 12 and the core component 14 are installed in the intervertebral space, bone graft material held in the bone graft material receiving spaces 44 passes through the two apertures 21 in the superior component to thereby help provide for fusion with the adjacent vertebra. Likewise, bone graft material held in the bone graft material receiving spaces 44 passes through two apertures in the inferior component 16, which is described below.

The core component 14 defines integrally formed structures on each of the upper side 40 and the lower side 42. The structures on the upper side 40 of the core component 14 comprise first and second anterior protrusions 48 and first and second posterior protrusions 50. The first and second anterior protrusions 48 extend up from the upper surface and at the anterior edge of the core component 14 but within the anterior boundary and such that they are spaced apart from each other in the transverse direction. As can be seen from FIG. 1D, the posterior facing side of each of the first and second anterior protrusions 48 is inclined to a plane in which the anterior-posterior direction and the transverse direction lie whereby the base of the posterior facing side slopes up and away from the anterior side. The first and second posterior protrusions 50 extend from the posterior side of the core component 14 and such that an upper side of each posterior protrusion is an extension of and lies in the same plane as the upper surface 40. Furthermore, the first and second posterior protrusions 50 are spaced apart from each other in the transverse direction. Each of the first and second posterior protrusions 50 is defined by the extension of the upper side 40 which terminates in an elongate sharp edge and by a lower side of the protrusion which extends away from the elongate sharp edge to the posterior side of the core component 14. The lower side is inclined to a plane in which the anterior-posterior direction and the transverse direction lie whereby the lower side is sloped between the elongate sharp edge and the posterior side.

The structures on the upper side 40 of the core component 14 further comprise a first channel which extends between the anterior and posterior ends of the core component such that it bisects the core component. A recess 52 is defined in each of the opposing walls of the first channel and such that the recesses are in registration with each other and near the anterior end of the core component. Each recess 52 is shaped to receive a respective one of the protrusions 36 on the first and second superior cantilever spring structures 34.

The core component 14 is brought into inter-engagement with the superior component 12 by first fitting the posterior end of the core component between the anterior ends of the first and second straight walls 26, 28 of the superior component. The width of the core component 14 in the transverse direction and the spacing apart of the first and second straight walls 26, 28 is such that the core component is a snug fit between the first and second straight walls whilst allowing for sliding relative movement of the core and superior components. As the posterior end of the core component is fitted between anterior ends of the first and second straight walls 26, 28, the ends of the first and second superior cantilever spring structures 34 abut against respective curved edges of the first channel in the core component. The core component 14 is then slid in the posterior direction such that there is a progressive increase in an extent of overlap of the core and superior components as the posterior end of the core component moves towards the posterior end of the superior component. As the core component 14 is slid in the posterior direction, the ends of the first and second superior cantilever spring structures 34 travel along the curving together walls of the first channel whereby the ends of the first and second superior cantilever spring structures are pressed towards each other and thereby develop spring bias.

As the posterior end of the core component approaches the posterior end of the superior component, the elongate sharp edges of the first and second posterior protrusions 50 are received in their respective first and second posterior recesses 32. Further movement of the posterior end of the core component towards the posterior end of the superior component causes the sloped lower side of each of the first and second posterior protrusions 50 to ride up over the slope defined by a respective one of the first and second posterior recesses 32 whereby the posterior end of the core component and the posterior end of the superior component are drawn together. Furthermore, and as the posterior end of the core component approaches the posterior end of the superior component, the first and second anterior protrusions 48 are received in their respective first and second anterior recesses 30. Further movement of the posterior end of the core component towards the posterior end of the superior component causes the sloped posterior facing side of each of the first and second anterior protrusions 48 to ride up the sloped base of each of the first and second anterior recesses 30 whereby the anterior end of the core component and the anterior end of the superior component are drawn together.

When the posterior end of the core component is approaching full reception at the posterior end of the superior component, the protrusion 36 on each of the first and second superior cantilever spring structures 34 starts to be received in a respective one of the two recesses 52 defined in the opposing walls of the first channel in the core component. Each protrusion 36 is urged into its respective recess 52 by the spring bias of the respective one of the first and second superior cantilever spring structures 34. When the protrusions 36 are fully received in their respective recesses 52 upon full reception of the posterior end of the core component at the posterior end of the superior component, the spring bias of the first and second superior cantilever spring structures 34 presents resistance to ejection of the protrusions 36 from the recesses 52. Furthermore, each protrusion 36 and each recess 52 is shaped for movement of their surfaces over each other to allow for ease of reception of protrusion in recess as the core component moves in the posterior direction and for their surfaces to abut against each other to present a barrier against ejection of protrusion from recess upon application of force liable to move the core component in the opposite, anterior direction. The superior and core components 12, 14 are thus structured to present resistance to ejection of the core component in the anterior direction relative to the superior component when the anterior lumbar interbody fusion device 10 is in situ in the intervertebral space.

Referring now to FIG. 1E in particular, structures on the lower side 42 of the core component 14 comprise a second channel which extends between the anterior and posterior ends of the core component such that it bisects the core component. First and second sets of plural recesses 54 are defined in each of the opposing walls of the second channel. The plural recesses 54 defined in each wall are equally spaced apart in the anterior-posterior direction. Also, the set of plural recesses 54 in one wall are in registration with the set of plural recesses 54 in the other wall such that each recess in one wall is in registration with a recess in the other wall. The plural recesses 54 in each wall are shaped to form a toothed rack which permits movement of a protrusion comprised in the inferior component 16 in the anterior direction only of the posterior and anterior directions. The structures on the lower side 42 of the core component 14 further comprise first and second ledges 56. Each ledge 56 projects in the transverse direction from a respective transverse side of the core component 14 and extends between the anterior and posterior sides of the core component. Each ledge 56 projects from its transverse side with one side of the ledge being planar with and an extension of the lower side 42 of the core component whereby the ledge projects from an edge between the transverse side and the lower side 42 of the core component.

Turning now to FIGS. 1F and 1G, the inferior component 16 is integrally formed from a metal or plastics material and has an inferior component top side 60 and an inferior component bottom side 62. The inferior component 16 is of a size such that it can be received in the intervertebral space whereby the inferior component bottom side 62 abuts against the lower vertebra. The inferior component 16 defines two apertures 64 which extend therethrough and are spaced apart from each other in the transverse direction. The two apertures 64 allow for passage of bone graft material from inside the anterior lumbar interbody fusion device 10. The inferior component 16 has an integrally formed inferior lug 66 which extends from an anterior end of the inferior component and substantially orthogonally to the inferior component bottom side 62 such that the inferior lug extends above the inferior component bottom side. The inferior lug 66 defines two inferior lug apertures 68 extending therethrough. The two inferior lug apertures 68 are spaced apart in the transverse direction. As described above, the surgeon aligns the inferior component 16 with the lower vertebra and fixes the inferior component 16 to the lower vertebra with screws. Screw fixing is done either when the superior and inferior components are first inserted into the intervertebral space or after correction of the spondylolisthesis. Considering this part of the surgical procedure further, the inferior component 16 is aligned with the lower vertebra by moving the inferior component 16 into the intervertebral space in the posterior direction until the inferior lug 66 abuts against the anterior aspect of the lower vertebra. The surgeon then drives a screw through each of the inferior lug apertures 68 and into the lower vertebra to fix the inferior component 16 to the lower vertebra.

Considering FIG. 1F in particular, the inferior component 16 defines integrally formed structures at the inferior component top side 60. The structures comprise first and second walls 70, 72 which each extend up from the inferior component top side 60 and away from the inferior component bottom side 62. Each of the first and second walls 70, 72 is towards a respective transverse side of the inferior component 16 such that the first and second walls are parallel and face each other. The first and second walls 70, 72 run in the anterior-posterior direction. Each of the first and second walls 70, 72 defines a channel 74 which extends along the length of the wall in the anterior-posterior direction.

The structures at the inferior component top side 60 yet further comprise first and second inferior cantilever spring structures 76. Each inferior cantilever spring structure 76 comprises a cantilever spring member which extends at its proximal end from near the posterior end of the inferior component 16 to near the anterior end of the inferior component. A protrusion 78 projects in the transverse direction from towards a distal end of the inferior cantilever spring member. The two inferior cantilever spring members are substantially parallel and each of the inferior cantilever spring members is substantially parallel with and facing a respective one of the first and second straight walls 70, 72. The first and second inferior cantilever spring structures 76 are located on a respective side of a line which bisects the inferior component 16 and which extends in the anterior-posterior direction whereby the first and second inferior cantilever spring structures are spaced apart to a small extent from each other in the transverse direction. Furthermore, the protrusions 78 project in opposite directions from their respective inferior cantilever spring members towards their respective first and second straight walls 70, 72. As described further below, each of the protrusions 78 on the first and second inferior cantilever spring structures 76 is received in a respective recess 54 defined by the core component 14 to lock the inferior component 16 and the core component together.

As described above, the surgical procedure involves inserting the superior and inferior components 12, 16 into the intervertebral space and inserting the core component 14 between the superior and inferior components with there being inter-engagement between core component and superior component and inter-engagement between core component and inferior component. Inter-engagement between inferior and core components 16, 14 involves the posterior end of the core component 14 being fitted between the anterior ends of the first and second walls 70, 72 of the inferior component 16 such that each ledge 56 is slidably received in a respective channel 74. As the posterior end of the core component 14 is fitted in this fashion, the ends of the first and second inferior cantilever spring structures 76 abut against respective curved edges of the second channel in the core component. The core component 14 is then slid in the posterior direction such that there is a progressive increase in an extent of overlap of the core and inferior components as the posterior end of the core component moves towards the posterior end of the inferior component. As the core component 14 is slid in the posterior direction, the ends of the first and second inferior cantilever spring structures 76 travel along the curving together walls of the second channel whereby the ends of the first and second inferior cantilever spring structures are pressed towards each other and thereby develop spring bias.

As the core component 14 and inferior component 16 are approaching about fifty percent overlap with each other, the protrusion 78 on each of the first and second inferior cantilever spring structures 76 is received under spring bias in a first recess in a respective one of the first and second sets of plural recesses 54. As described above, the plural recesses 54 in each set of plural recesses are shaped to form a toothed rack which in view of the corresponding shape of the protrusion 78 permits movement of the protrusion relative to the toothed rack in the anterior direction only of the posterior and anterior directions. The two sets of plural recesses 54 and the first and second inferior cantilever spring structures 76 constitute the first locking mechanism. The surgeon can therefore cease applying force to reduce the extent of spondylolisthesis whereupon operation of the first locking mechanism presents resistance to movement of the core component in the posterior, spondylolisthesis increasing direction.

As overlap of the core and inferior components 14, 16 increases beyond fifty percent, the protrusion 78 on each of the first and second inferior cantilever spring structures 76 is received under spring bias in successive recesses in a respective one of the first and second sets of plural recesses 54. The surgeon can therefore reduce the extent of spondylolisthesis stage by stage until the spondylolisthesis is properly reduced with operation of the first locking mechanism at each stage of reduction presenting resistance to spondylolisthesis increasing movement. FIG. 1H shows the anterior lumbar interbody fusion device 10 before correction of a Grade 2 spondylolisthesis. FIG. 1I shows the anterior lumbar interbody fusion device 10 after correction of the spondylolisthesis.

The first embodiment of anterior lumbar interbody fusion device 10 has dimensions appropriate for use as such. The superior component has a range of length by width from 20 mm by 20 mm to 50 mm by 50 mm. The superior component has a range of height at the posterior end from 1 mm to 4 mm. The inferior component has a range of length by width from 20 mm by 20 mm to 50 mm by 50 mm. The inferior component has a range of height at the posterior end from 1 mm to 4 mm. The core component has a range of length by width from 20 mm by 20 mm to 50 mm by 50 mm. The core component has a range of height at the posterior end from 4 mm to 10 mm.

Figure 2F:
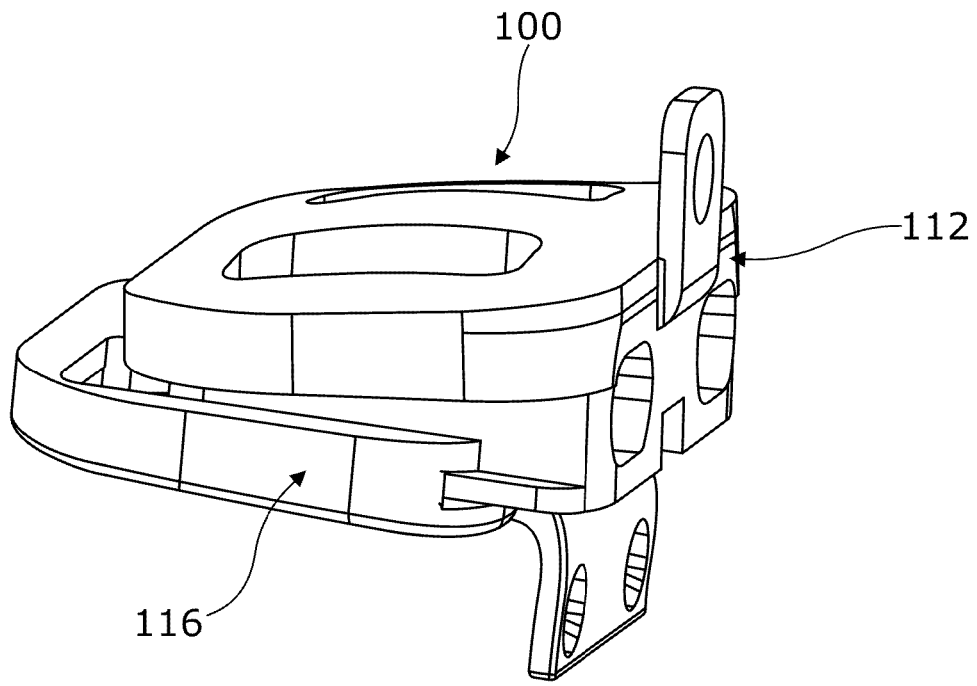
FIG. 2F is a perspective view from above of the second embodiment of anterior lumbar interbody fusion device when assembled and before correction of spondylolisthesis.
Figure 2G:
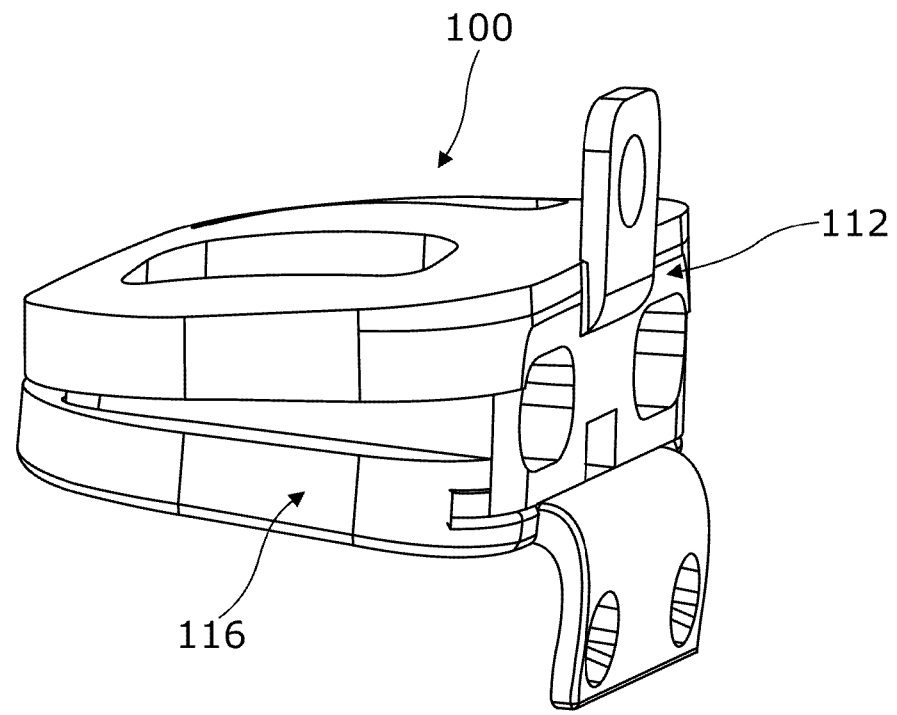
FIG. 2G is a perspective view from above of the second embodiment of anterior lumbar interbody fusion device when assembled and after correction of spondylolisthesis.

A second embodiment of anterior lumbar interbody fusion device 100 is shown in FIGS. 2A to 2G. As described above in respect of the first embodiment, the present embodiment of anterior lumbar interbody fusion (ALIF) device is introduced into a patient's intervertebral space between first and second adjacent vertebrae from the anterior side of the patient. The second embodiment of anterior lumbar interbody fusion device 100 comprises a superior component 112 and an inferior component 116. Perspective views of the superior component 112 from below and above are shown respectively in FIGS. 2A and 2B. A view of the superior component 112 from below is shown in FIG. 2C. Perspective views of the inferior component 116 from above and below are shown respectively in FIGS. 2D and 2E. FIG. 2F is a perspective view from above of the second embodiment of anterior lumbar interbody fusion device 100 when assembled and installed in an intervertebral space of a patient and before correction of spondylolisthesis. FIG. 2F shows the anterior lumbar interbody fusion device 100 before correction of a Grade 2 spondylolisthesis. FIG. 2G is a perspective view from above of the second embodiment of anterior lumbar interbody fusion device 100 when assembled and after correction of the spondylolisthesis. As may be appreciated from inspection of FIGS. 2A to 2G, the second embodiment of anterior lumbar interbody fusion device 100 lacks the core component of the first embodiment with the core component of the first embodiment being, in effect, an integral part of the superior component 112.

The inferior component 116 is generally of the form of a plate, albeit a plate having structures thereon and two spaced apart apertures therethrough. The superior component 112 has the form of a frustum of a wedge. The second embodiment of anterior lumbar interbody fusion device 100 is assembled and installed in the intervertebral space first by insertion of the inferior component 116 into the intervertebral space with the inserted inferior component being fixed with screws to the lower or second vertebra either at this stage or after the spondylolisthesis has been corrected. Then the superior component 112 is inserted into the intervertebral space. When the superior component 112 is being inserted into the intervertebral space, the superior component is aligned with the inferior component 116 such that the superior component slidably inter-engages with the inferior component. The superior component 112 is then moved in the posterior direction relative to the inferior component 116 such that the extent of overlap of the superior and inferior components 112, 116 increases until the superior component 112 is aligned with the upper or first vertebra. The surgeon then fixes the superior component 112 with a screw to the upper vertebra. Alternatively screw fixing is after the spondylolisthesis has been corrected. At this stage in the procedure, the anterior lumbar interbody fusion device 100 has the disposition shown in FIG. 2F which reflects the extent of spondylolisthesis before correction. The surgeon then manipulates the patient to correct the spondylolisthesis with this involving further movement of the superior component 112 in the posterior direction relative to the inferior component 116 to increase the extent of overlap of the superior and inferior components until the spondylolisthesis is corrected. At this stage in the procedure, the anterior lumbar interbody fusion device 100 has the disposition shown in FIG. 2G. As described further below, the anterior lumbar interbody fusion device 100 is configured to resist spondylolisthesis increasing movement of the superior component 112 in the anterior direction.

Turning now to FIGS. 2A to 2C, the superior component 112 is integrally formed from a metal or plastics material and has a superior component top side 118 and a superior component bottom side 120. The superior component 112 is of a size such that it can be received in the intervertebral space whereby the superior component top side 118 abuts against the upper vertebra. The superior component 112 defines two apertures 121 which extend therethrough and are spaced apart from each other in the transverse direction. The two apertures 121 allow for passage of bone graft material from inside the anterior lumbar interbody fusion device 100. The superior component 112 has an integrally formed superior lug 122 which extends from an anterior end of the superior component and substantially orthogonally to the superior component top side 118 such that the superior lug extends above the superior component top side. The superior lug 122 defines a superior lug aperture 124 extending therethrough. As described above, the surgeon aligns the superior component 112 with the upper vertebra and fixes the superior component 112 with a screw to the upper vertebra either during the procedure or after the spondylolisthesis has been corrected. Considering this latter part of the surgical procedure further, the superior component 112 is aligned with the upper vertebra by moving the superior component 112 in the posterior direction into the intervertebral space until the superior lug 122 abuts against the anterior aspect of the upper vertebra. The surgeon then drives the screw through the superior lug aperture 124 and into the upper vertebra to fix the superior component 112 to the upper vertebra.

As may be appreciated from FIG. 2B, the superior component top side 118 and the superior component bottom side 120 are inclined to each other and do not meet at an acute angle whereby the superior component 112 has the form of a frustum of a wedge with the thickest part of the wedge at the anterior side of the superior component. Furthermore, the superior component 116 defines two bone graft material receiving spaces 144 which are spaced apart from each other in the transverse direction with each bone graft material receiving space extending up from the superior component bottom side 120 to their respective apertures 121 at the superior component top side 118. Two spaced apart bone graft material receiving apertures 146 are defined in the anterior side of the superior component 112 such that they are spaced apart from each other in the transverse direction. Each bone graft material receiving aperture 146 is in fluid communication with a respective one of the two bone graft material receiving spaces 144 whereby bone graft material can be introduced into the receiving space 144 by way of the bone graft material receiving aperture. When the superior component 112 is installed in the intervertebral space, bone graft material held in the bone graft material receiving spaces 144 passes through the two apertures 121 in the superior component to thereby help provide for fusion with the adjacent vertebra. Likewise, bone graft material held in the bone graft material receiving spaces 144 passes through two apertures in the inferior component 116. The inferior component 116 is described below.

Considering FIGS. 2A and 2B in particular, the superior component 12 defines integrally formed structures at the superior component bottom side 120. The structures on the superior component bottom side 120 comprise a channel which extends between the anterior and posterior ends of the superior component such that it bisects the superior component. First and second sets of plural recesses 154 are defined in each of the opposing walls of the channel. The plural recesses 154 defined in each wall are equally spaced apart in the anterior-posterior direction. Also, the set of plural recesses 154 in one wall are in registration with the set of plural recesses 154 in the other wall such that each recess in one wall is in registration with a recess in the other wall. The plural recesses 154 in each wall are shaped to form a toothed rack which permits movement of a protrusion comprised in the inferior component 116 in the anterior direction only of the posterior and anterior directions. The superior component bottom side 120 further comprise first and second ledges 156. Each ledge 156 projects in the transverse direction from a respective transverse side of the superior component 112 and extends between the anterior and posterior sides of the superior component. Each ledge 156 projects from its transverse side with one side of the ledge being planar with and an extension of the superior component bottom side 120 whereby the ledge projects from an edge between the transverse side and the superior component bottom side 120.

Turning now to FIGS. 2D and 2E, the inferior component 116 of the present embodiment is integrally formed from a metal or plastics material and is of the same form as the inferior component 16 of the first embodiment. Features of the inferior component 116 of the second embodiment are designated with reference numerals in common with features of the inferior component 16 of the first embodiment. The reader's attention in respect of features of the inferior component 116 of the second embodiment is therefore directed to the description of the inferior component 16 of the first embodiment provided above with reference to FIGS. 1F and 1G.

As described above, the surgical procedure involves installing the inferior component 116 in the intervertebral space. The superior component 112 is then brought into inter-engagement with the inferior component 116 installed in the intervertebral space. Alternatively, the superior component 112 is brought into preliminary inter-engagement with the inferior component 116 before they are both installed in the intervertebral space. The superior component 112 is brought into inter-engagement with the inferior component 116 by positioning the posterior side of the superior component in front of and relative to the anterior side of the inferior component 116. The posterior end of the superior component 112 is fitted between the anterior ends of the first and second walls 70, 72 of the inferior component 116 such that each ledge 156 is slidably received in a respective channel 74. As the posterior end of the superior component 112 is fitted in this fashion, the ends of the first and second inferior cantilever spring structures 76 abut against respective curved edges of the channel in the superior component. The superior component 112 is then slid in the posterior direction such that there is a progressive increase in an extent of overlap of the superior and inferior components as the posterior end of the superior component moves towards the posterior end of the inferior component. As the superior component 112 is slid in the posterior direction, the ends of the first and second inferior cantilever spring structures 76 travel along the curving together walls of the channel whereby the ends of the first and second inferior cantilever spring structures are pressed towards each other and thereby develop spring bias.

As the superior component 112 and the inferior component 116 are approaching about fifty percent overlap with each other, the protrusion 78 on each of the first and second inferior cantilever spring structures 76 is received under spring bias in a first recess in a respective one of the first and second sets of plural recesses 154. As described above, the plural recesses 154 in each set are shaped to form a toothed rack which in view of the corresponding shape of the protrusion 78 permits movement of the protrusion relative to the toothed rack in the anterior direction only of the posterior and anterior directions. The two sets of plural recesses 154 and the first and second inferior cantilever spring structures 76 constitute the first locking mechanism. The surgeon can therefore cease applying force to reduce the extent of spondylolisthesis whereupon operation of the first locking mechanism presents resistance to movement of the core component in the posterior, spondylolisthesis increasing direction.

As overlap of the superior and inferior components 112, 116 increases beyond fifty percent, the protrusion 78 on each of the first and second inferior cantilever spring structures 76 is received under spring bias in successive recesses in a respective one of the first and second sets of plural recesses 154. The surgeon can therefore reduce the extent of spondylolisthesis stage by stage until the spondylolisthesis is properly reduced with operation of the first locking mechanism at each stage of reduction presenting resistance to spondylolisthesis increasing movement. FIG. 2F shows the second embodiment of anterior lumbar interbody fusion device 100 before correction of a Grade 2 spondylolisthesis. FIG. 2G shows the second embodiment of anterior lumbar interbody fusion device 100 after correction of the spondylolisthesis.

The second embodiment of anterior lumbar interbody fusion device 100 has dimensions appropriate for use as such. The superior component has a range of length by width from 20 mm by 20 mm to 50 mm by 50 mm. The superior component has a range of height at the posterior end from 4 mm to 14 mm. The inferior component has a range of length by width from 20 mm by 20 mm to 50 mm by 50 mm. The inferior component has a range of height at the posterior end from 1 mm to 4 mm.

Figure 3A:
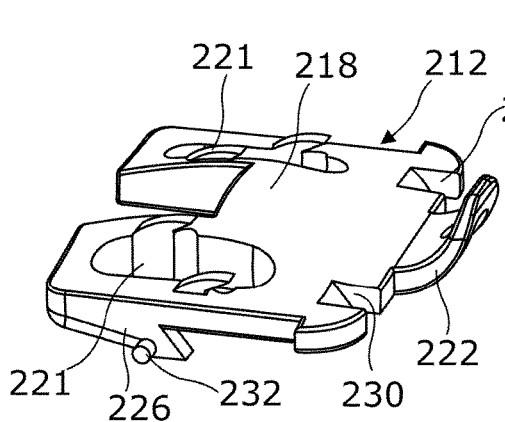
FIG. 3A is a perspective view from above of the superior component of a third embodiment of anterior lumbar interbody fusion device.
Figure 3B:
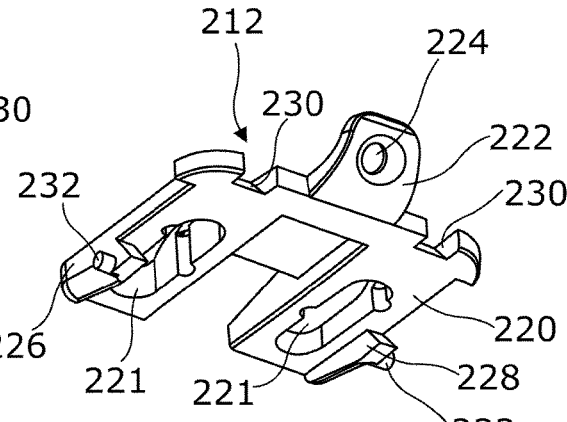
FIG. 3B is a perspective view from below of the superior component of FIG. 3A.
Figure 3C:
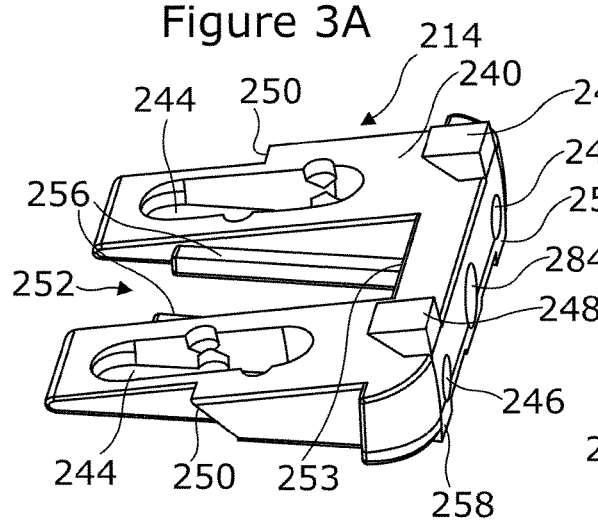
FIG. 3C is a perspective view from above of the core component of the third embodiment of anterior lumbar interbody fusion device.
Figure 3D:
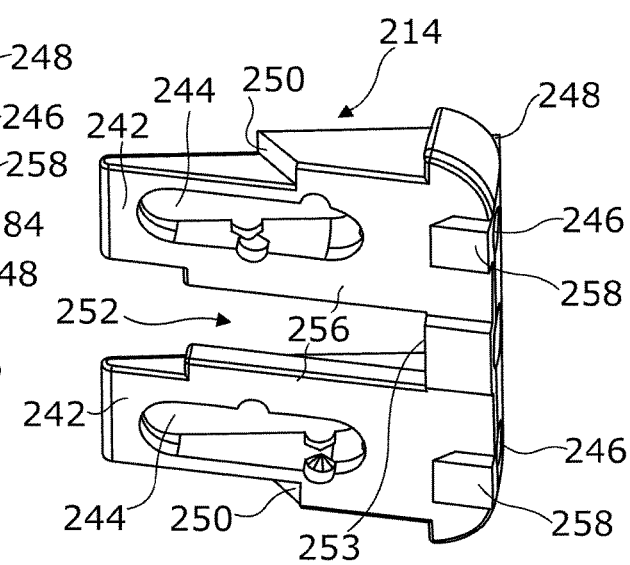
FIG. 3D is a perspective view from below of the core component of FIG. 3C.
Figure 3E:
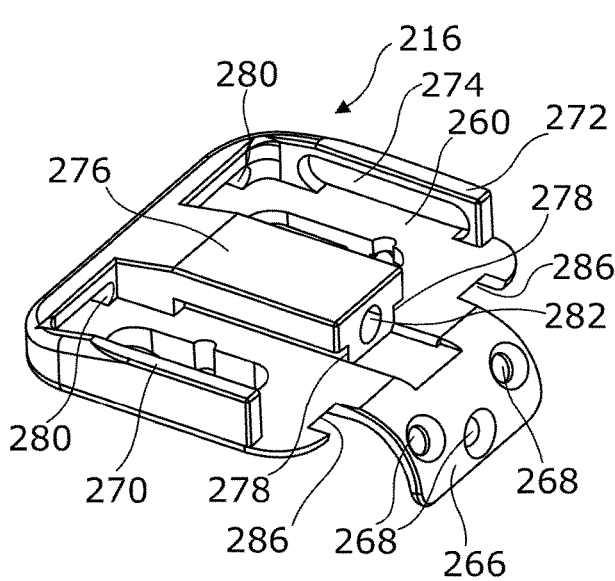
FIG. 3E is a perspective view from above of the inferior component of the third embodiment of anterior lumbar interbody fusion device.
Figure 3F:
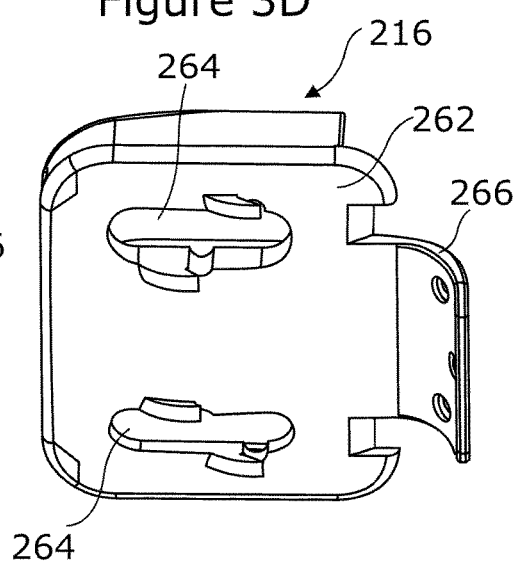
FIG. 3F is a perspective view from below of the inferior component of FIG. 3E.
Figure 3G:
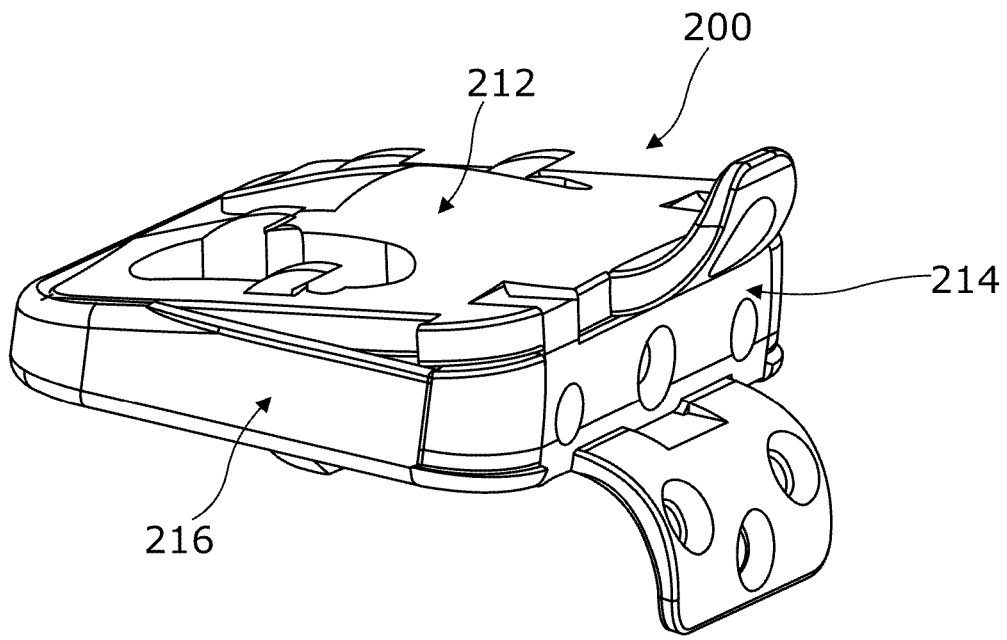
FIG. 3G is a perspective view from above of the third embodiment of anterior lumbar interbody fusion device when assembled and after correction of spondylolisthesis.
Figure 3H:
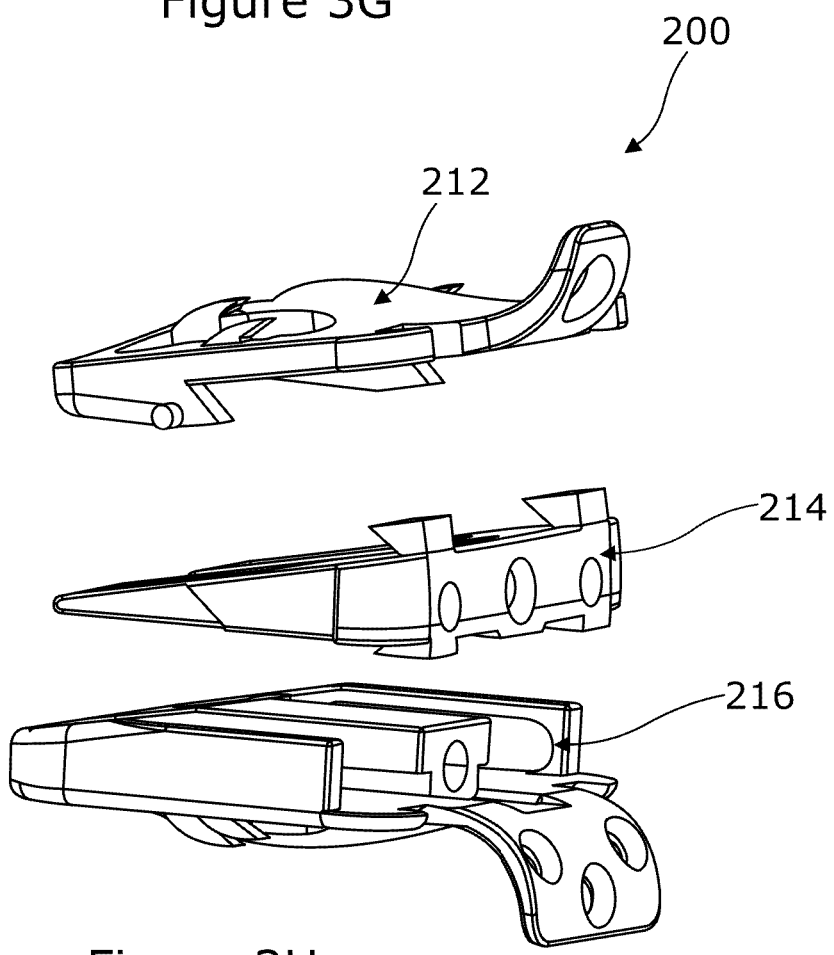
FIG. 3H is an exploded perspective view of the third embodiment of anterior lumbar interbody fusion device.

A third embodiment of anterior lumbar interbody fusion device 200 is shown in FIGS. 3A to 3H. As described above in respect of the first embodiment, the present embodiment of anterior lumbar interbody fusion (ALIF) device is introduced into a patient's intervertebral space between first and second adjacent vertebrae from the anterior side of the patient. The third embodiment of anterior lumbar interbody fusion device 200 comprises a superior component 212, a core component 214 and an inferior component 216. Perspective views of the superior component 212 from above and below are shown respectively in FIGS. 3A and 3B. Perspective views of the core component 214 from above and below are shown respectively in FIGS. 3C and 3D. Perspective views of the inferior component 216 from above and below are shown respectively in FIGS. 3E and 3F. FIG. 3G is a perspective view from above of the third embodiment of anterior lumbar interbody fusion device 200 when assembled and installed in an intervertebral space of a patient and after correction of spondylolisthesis. FIG. 3H is an exploded perspective view of the third embodiment of anterior lumbar interbody fusion device 200.

As may be appreciated from inspection of FIGS. 3A to 3H, the third embodiment in common with the first embodiment of anterior lumbar interbody fusion device 200 comprises a core component. Otherwise, the third embodiment is structured differently from the first embodiment, as will now be described.

Each of the superior component 212 and the inferior component 216 is generally of the form of a plate, albeit a plate having structures thereon and two spaced apart apertures therethrough. The core component 214 has the form of a wedge. The anterior lumbar interbody fusion device 200 is assembled and installed in the intervertebral space first by bringing the superior component 212 and the inferior component 216 into inter-engagement with each other before they are inserted into the intervertebral space. Upon insertion or after correction of the spondylolisthesis, the inferior component 216 is fixed with three screws to the lower or second vertebra. The core component 214 is then inserted between the superior and inferior components 212, 216. When the core component 214 and the superior component 212 are fully inter-engaged, they move together in the intervertebral space relative to the inferior component 216 with the core component slidably inter-engaging with the inferior component. Movement of the superior and core components 212, 214 together in the posterior direction relative to the inferior component 16 increases the extent of overlap of the superior and inferior components 212, 216 until the superior component 212 is aligned with the upper or first vertebra. The surgeon then fixes the superior component 212 with a screw to the upper vertebra. Alternatively, screw fixing is done after correction of the spondylolisthesis. The surgeon then manipulates the patient to correct the spondylolisthesis with this involving further movement of the superior and core components 212, 214 together in the posterior direction relative to the inferior component 216 by way of the screw threaded locking mechanism described below to increase the extent of overlap of the superior and inferior components until the spondylolisthesis is corrected. At this stage in the procedure, the third embodiment of anterior lumbar interbody fusion device 200 has the disposition shown in FIG. 3G. As will become clear from the following description, the third embodiment of anterior lumbar interbody fusion device 200 is configured to resist spondylolisthesis increasing movement of the superior and core components 212, 214 together in the anterior direction.

Turning now to FIGS. 3A and 3B, the superior component 212 is integrally formed from a metal or plastics material and has a superior component top side 218 and a superior component bottom side 220. The superior component 212 is of a size such that it can be received in the intervertebral space whereby the superior component top side 218 abuts against the upper vertebra. The superior component 212 defines two apertures 221 which extend therethrough and are spaced apart from each other in the transverse direction. The two apertures 221 allow for passage of bone graft material from inside the anterior lumbar interbody fusion device 200. The superior component 212 has an integrally formed superior lug 222 which extends from an anterior end of the superior component and substantially orthogonally to the superior component top side 218 such that the superior lug extends above the superior component top side. The superior lug 222 defines a superior lug aperture 224 extending therethrough. As described above, the surgeon aligns the superior component 212 with the upper vertebra and fixes the superior component 212 with a screw to the upper vertebra either during the procedure or after correction of the spondylolisthesis. Considering this latter part of the surgical procedure further, the superior component 212 is aligned with the upper vertebra by moving the superior component 212 in the posterior direction in the intervertebral space until the superior lug 222 abuts against the anterior aspect of the upper vertebra. The surgeon drives the screw through the superior lug aperture 224 and into the upper vertebra to fix the superior component 212 to the upper vertebra.

Considering FIG. 3B in particular, the superior component 212 defines integrally formed structures at the superior component bottom side 220. The structures comprise first and second straight walls 226, 228 which each extend up from the superior component bottom side 220 and away from the superior component top side 218. Each of the first and second walls 226, 228 is towards a respective transverse side of the superior component 212 such that the first and second walls are parallel and face each other. The first and second walls 226, 228 run in the anterior-posterior direction from the posterior end of the superior component 212 halfway towards the anterior end of the superior component. An anterior facing end of each of the first and second walls 226, 228 slopes from the superior component bottom side 220 in a direction towards the posterior end of the core component. As described further below, the first and second walls provide for slidable engagement with the core component 214 and guide movement of the core component relative to the superior component 212 before providing for inter-engagement with the superior component.

The structures in the superior component 212 comprise first and second anterior recesses 230 and first and second cylindrical protrusions 232. The first and second anterior recesses 230 are defined in the anterior edge of the superior component 212 and such that they are spaced apart from each other in the transverse direction. As can be seen from FIG. 3A, the base of each of the first and second anterior recesses 230 is inclined to a plane in which the anterior-posterior direction and the transverse direction lie whereby the base of the recess slopes upwards away from the anterior side. As described further below, a sloped surface of a corresponding protrusion on the core component 214 rides over the sloped base of each anterior recess 230 to draw the core component and superior component together and into inter-engagement. Each of the first and second cylindrical protrusions 232 extends from the outside of a respective one of the first and second walls 226, 228 whereby the first and second cylindrical protrusions 232 lie on the same axis and extend in opposite directions and in the transverse direction. As described further below, the first and second cylindrical protrusions 232 inter-engage with the inferior component 216 and provide for relative movement of the superior component 212 and inferior component 216 in the anterior-posterior direction and for limited relative movement of the superior and inferior components in the direction of separation of the superior and inferior components.

Turning now to FIGS. 3C and 3D, the core component 214 is integrally formed from a metal or plastics material and has an upper side 240 and a lower side 242. As can be seen from FIG. 3H, the upper side 240 and the lower side 242 are inclined to each other and meet at a rounded acute angle whereby the thickest part of the wedge is at the anterior side of the core component. The core component defines two bone graft material receiving spaces 244 which are spaced apart from each other in the transverse direction with each bone graft material receiving space extending from the upper side 240 to the lower side 242. Two spaced apart bone graft material receiving apertures 246 are defined in the anterior side of the core component 214 such that they are spaced apart from each other in the transverse direction.

Each bone graft material receiving aperture 246 is in fluid communication with a respective one of the two bone graft material receiving spaces 244 whereby bone graft material can be introduced into the receiving space 244 by way of the bone graft material receiving aperture. When the superior component 212 and the core component 214 are installed in the intervertebral space, bone graft material held in the bone graft material receiving spaces 244 passes through the two apertures 221 in the superior component to thereby help provide for fusion with the adjacent vertebra. Likewise, bone graft material held in the bone graft material receiving spaces 244 passes through two apertures in the inferior component 216, which is described below.

The core component 214 defines integrally formed structures on each of the upper side 240 and the lower side 242. The structures on the upper side 240 of the core component 214 comprise first and second anterior protrusions 248. The first and second anterior protrusions 248 extend up from the upper surface and at the anterior edge of the core component 214 but within the anterior boundary and such that they are spaced apart from each other in the transverse direction. As can be seen from FIGS. 3C and 3D, the posterior facing side of each of the first and second anterior protrusions 248 is inclined to a plane in which the anterior-posterior direction and the transverse direction lie whereby the posterior facing side slopes up and away from the anterior side. The core component 214 also defines first and second shoulders 250 each at a respective transverse side of the core component. The first and second shoulders 250 are halfway along the core component between the anterior and posterior ends. The first and second shoulders 250 are aligned with each other. Each of the first and second shoulders 250 faces towards the posterior end of the core component and slopes upwards from the lower side 242 towards the posterior end.

The core component 214 is brought into inter-engagement with the superior component 212 by first fitting the posterior end of the core component between the ends of the first and second straight walls 226, 228 halfway along the superior component. The width of the core component 214 in the transverse direction and the spacing apart of the first and second straight walls 226, 228 is such that the core component is a snug fit between the first and second straight walls whilst allowing for sliding relative movement of the core and superior components. The core component 214 is then slid in the posterior direction such that there is a progressive increase in an extent of overlap of the core and superior components as the posterior end of the core component moves towards the posterior end of the superior component.

As the posterior end of the core component 214 approaches the posterior end of the superior component 212, the first and second anterior protrusions 248 are received in their respective first and second anterior recesses 230. Further movement of the posterior end of the core component towards the posterior end of the superior component causes the sloped posterior facing side of each of the first and second anterior protrusions 248 to ride up the sloped base of each of the first and second anterior recesses 230 whereby the anterior end of the core component and the anterior end of the superior component are drawn together. Furthermore, and as the posterior end of the core component 214 approaches the posterior end of the superior component 212, each of the first and second shoulders 250 abuts against the sloping anterior facing end of a respective one of the first and second walls 226, 228. Further movement of the posterior end of the core component towards the posterior end of the superior component causes the sloped first and second shoulders 250 to ride up the sloped anterior facing ends of the first and second walls 226, 228 whereby the core component and the superior component are drawn together. Thereafter the core component bears against the superior component by virtue of the first and second shoulders 250 whereby core component and superior component move together in the posterior direction.

The core component 214 defines a channel 252 which extends between and is open at the upper side 240 and the lower side 242. Furthermore, the channel 252 extends in the anterior-posterior direction such that it bisects the core component. The channel 252 terminates near the anterior end of the core component at a transversely extending boundary wall 253 and is open at the posterior end of the core component.

Referring now to FIG. 3D in particular, structures on the lower side 242 of the core component 214 comprise first and second ledges 256. Each ledge 256 projects in the transverse direction from a respective wall of the channel 252. Furthermore, each ledge 256 extends along its respective wall from the boundary wall 253 to about three quarters the distance from the boundary wall to the posterior end of the core component. Each ledge 256 is an extension of and planar with the lower side. The two ledges 256 therefore extend towards and are in registration with each other. The structures on the lower side 242 of the core component 214 also comprise third and fourth anterior protrusions 258. The third and fourth anterior protrusions 258 extend up from the lower surface and at the anterior edge of the core component 214 but within the anterior boundary and such that they are spaced apart from each other in the transverse direction. As can be seen from FIG. 3D, the posterior facing side of each of the third and fourth anterior protrusions 258 is inclined to a plane in which the anterior-posterior direction and the transverse direction lie whereby the posterior facing side slopes up and away from the anterior side.

Turning now to FIGS. 3E and 3F, the inferior component 216 is integrally formed from a metal or plastics material and has an inferior component top side 260 and an inferior component bottom side 262. The inferior component 216 is of a size such that it can be received in the intervertebral space whereby the inferior component bottom side 262 abuts against the lower vertebra. The inferior component 216 defines two apertures 264 which extend therethrough and are spaced apart from each other in the transverse direction. The two apertures 264 allow for passage of bone graft material from inside the anterior lumbar interbody fusion device 200. The inferior component 216 has an integrally formed inferior lug 266 which extends from an anterior end of the inferior component and substantially orthogonally to the inferior component bottom side 262 such that the inferior lug extends above the inferior component bottom side. The inferior lug 266 defines three inferior lug apertures 268 extending therethrough. The three inferior lug apertures 268 are spaced apart in the transverse direction. As described above, the surgeon aligns the inferior component 216 with the lower vertebra and fixes the inferior component 216 to the lower vertebra with screws either during the procedure or after correction of the spondylolisthesis. Considering this part of the surgical procedure further, the inferior component 216 is aligned with the lower vertebra by moving the inferior component 216 in the intervertebral space in the posterior direction until the inferior lug 266 abuts against the anterior aspect of the lower vertebra. The surgeon drives a screw through each of the three inferior lug apertures 268 and into the lower vertebra to fix the inferior component 216 to the lower vertebra.

Considering FIG. 3E in particular, the inferior component 216 defines integrally formed structures at the inferior component top side 260. The structures comprise first and second walls 270, 272 which each extend up from the inferior component top side 260 and away from the inferior component bottom side 262. Each of the first and second walls 270, 272 is at a respective transverse side of the inferior component 216 such that the first and second walls are parallel and face each other. The first and second walls 270, 272 run in the anterior-posterior direction. An elongate recess 274 is defined in the inside surface of each of the first and second walls 270, 272. Each elongate recess 274 extends a substantial distance between the anterior and posterior ends of the inferior component 216. The two elongate recesses 274 are in registration with and oppose each other. The inferior component 216 comprises an integrally formed island 276 of rectangular outline when viewed from the inferior component top side 260. The island 276 extends between the anterior and posterior ends of the inferior component and such that it is centrally disposed on a line which extends in the anterior-posterior direction and bisects the inferior component. The island 276 defines first and second elongate channels 278 in oppositely directed side walls of the island and such that the inferior component top side 260 constitutes the lower side of each channel. The channels 278 extend from the anterior end of the island 276 to near the posterior end of the island. The channels 278 are in registration with and face away from each other.

The inferior component 216 also defines first and second posterior recesses 280 which are defined at the proximal end of a posterior wall extending up from the inferior component top side 260. The first and second posterior recesses 280 are on opposite sides of the island 276 whereby the first and second posterior recesses are spaced apart from each other in the transverse direction. The island 276 defines a threaded bore 282 in the anterior end face of the island. The inferior component 216 also defines first and second anterior recesses 286. The first and second anterior recesses 286 are defined in the anterior edge of the inferior component 216 and such that they are spaced apart from each other in the transverse direction. As can be seen from FIG. 3F, the base of each of the first and second anterior recesses 286 is inclined to a plane in which the anterior-posterior direction and the transverse direction lie whereby the base of the recess slopes upwards away from the anterior side.

The surgical procedure involves either bringing the superior, core and inferior components 212, 214, 216 into inter-engagement with one another before they are installed in the intervertebral space or installing the superior and inferior components 212, 216 in the intervertebral space and inserting the core component 214 between the superior and inferior components. Irrespective of the approach followed, the superior and inferior components 212, 216 are attached to each other by fitting each one of the first and second cylindrical protrusions 232 into a respective one of the elongate recesses 274. When the superior and core components 212, 214 have been brought into preliminary inter-engagement, the core component is then brought into inter-engagement with the inferior component 216. The core component 214 is brought into inter-engagement with the inferior component 216 by positioning the posterior side of the core component in front of the anterior side of the inferior component 216. The small extent of movement of the first and second cylindrical protrusions 232 in their respective elongate recesses 274 allows for core components of different heights to be brought into use. The posterior end of the core component 214 is fitted between the anterior ends of the first and second walls 270, 272 of the inferior component 216 and such that each ledge 256 is slidably received in a respective channel 278. The core component 214 is then slid in the posterior direction such that there is a progressive increase in an extent of overlap of the core and inferior components as the posterior end of the core component moves towards the posterior end of the inferior component.

A threaded bolt (not shown) is fed through a bolt aperture 284, which extends through the centre of the anterior end of the core component 214 and is brought into threaded engagement with the threaded bore 282 in the anterior end face of the island 276. The threaded bolt is used to drive the core component 214 relative to the inferior component 216 against resistance presented by the spondylolisthesis to increase an extent of overlap of the core and inferior components and thereby reduce the extent of spondylolisthesis towards what is shown in FIG. 3G. The resistance presented by inter-engagement of the threaded bolt and the threaded bore 282 presents resistance to relative movement which would be liable to decrease extent of overlap of the core and inferior components, whereby the extent of spondylolisthesis can be decreased stage-by-stage by the surgeon as described above. As the posterior end of the core component 214 approaches the posterior end of the inferior component 216, each of the third and fourth anterior protrusions 258 on the core component is received in a respective one of the first and second anterior recesses 286 in the inferior component and such that their sloping surfaces ride over each other to draw and hold together the core and inferior components at their anterior ends. The first and second posterior recesses 280 in the inferior component receive anatomical matter and material sloughed from the anterior lumbar interbody fusion device 200 which might otherwise be liable to become trapped behind the core component 214 to thereby prevent the core component 214 being received fully between the superior and inferior components 212, 216.

The third embodiment of anterior lumbar interbody fusion device 200 has dimensions appropriate for use as such. The superior component has a range of length by width from 20 mm by 20 mm to 50 mm by 50 mm. The superior component has a range of height at the posterior end from 1 mm to 4 mm. The inferior component has a range of length by width from 20 mm by 20 mm to 50 mm by 50 mm. The inferior component has a range of height at the posterior end from 1 mm to 4 mm. The core component has a range of length by width from 20 mm by 20 mm to 50 mm by 50 mm. The core component has a range of height at the posterior end from 4 mm to 10 mm.

Figure 4A:
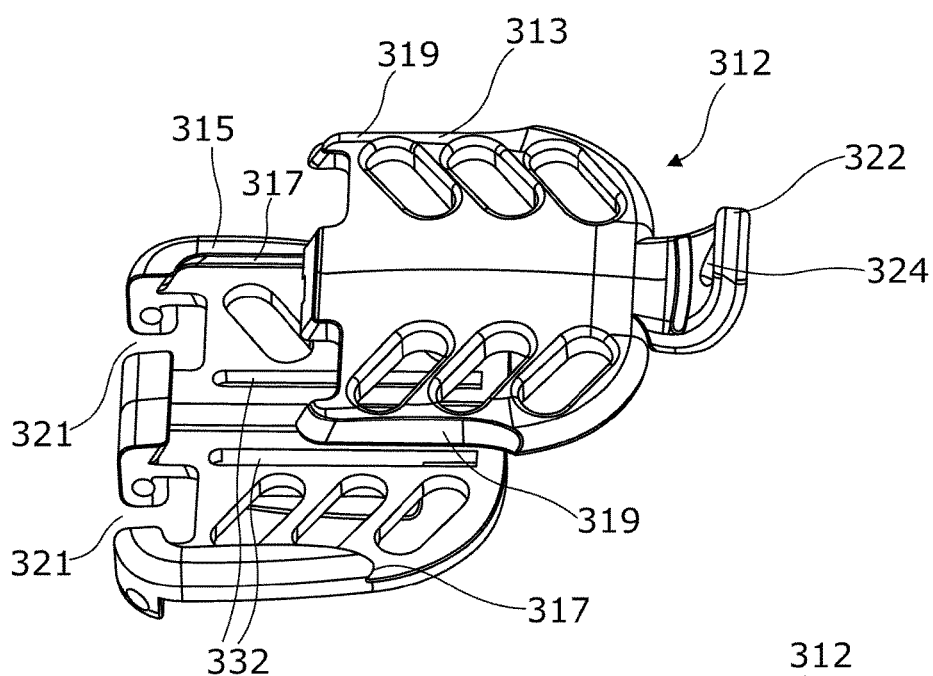
FIG. 4A is a perspective view from above of the superior component of a fourth embodiment of anterior lumbar interbody fusion device.
Figure 4B:
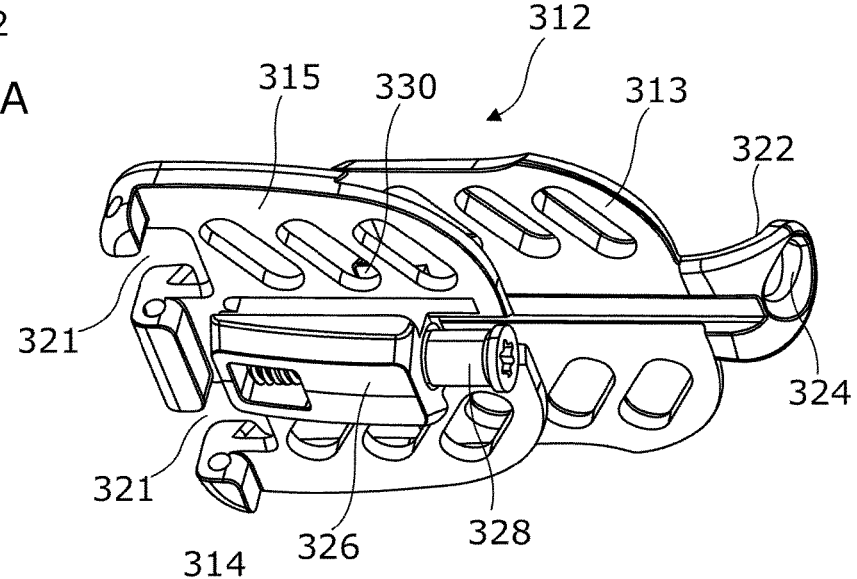
FIG. 4B is a perspective view from below of the superior component of FIG. 4A.
Figure 4C:
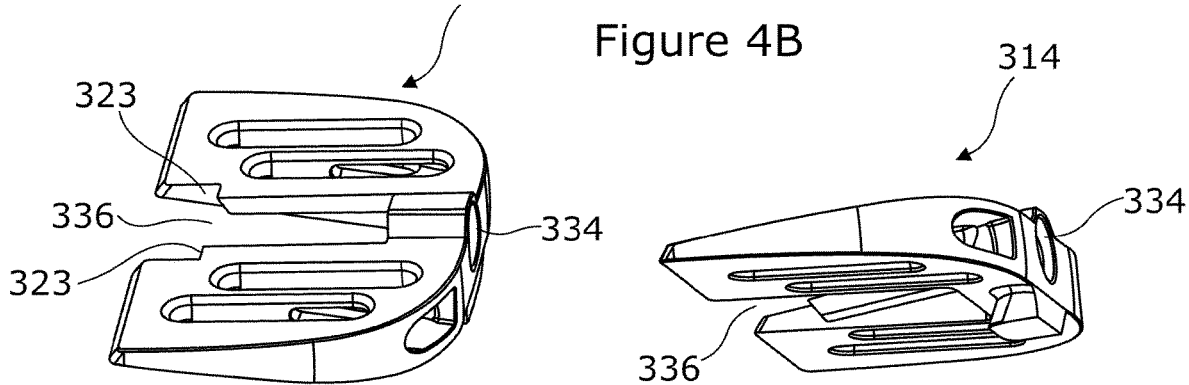
FIG. 4C is a perspective view from above of the core component of the fourth embodiment of anterior lumbar interbody fusion device.
Figure 4D:
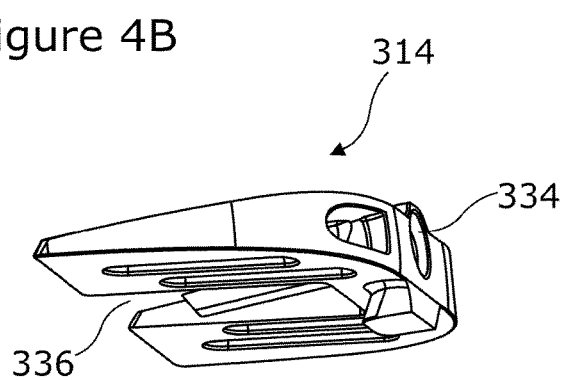
FIG. 4D is a perspective view from below of the core component of FIG. 4C.
Figure 4E:
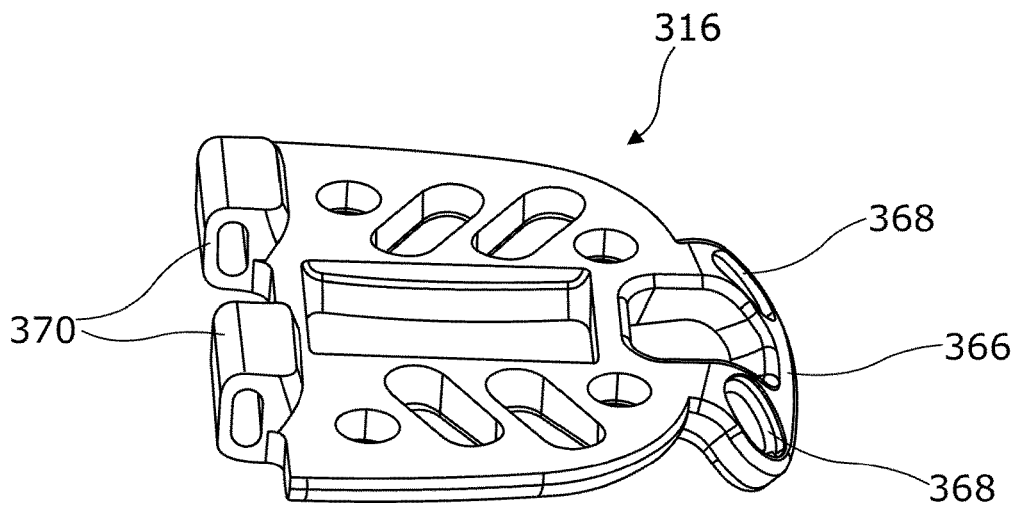
FIG. 4E is a perspective view from above of the inferior component of the fourth embodiment of anterior lumbar interbody fusion device.
Figure 4F:
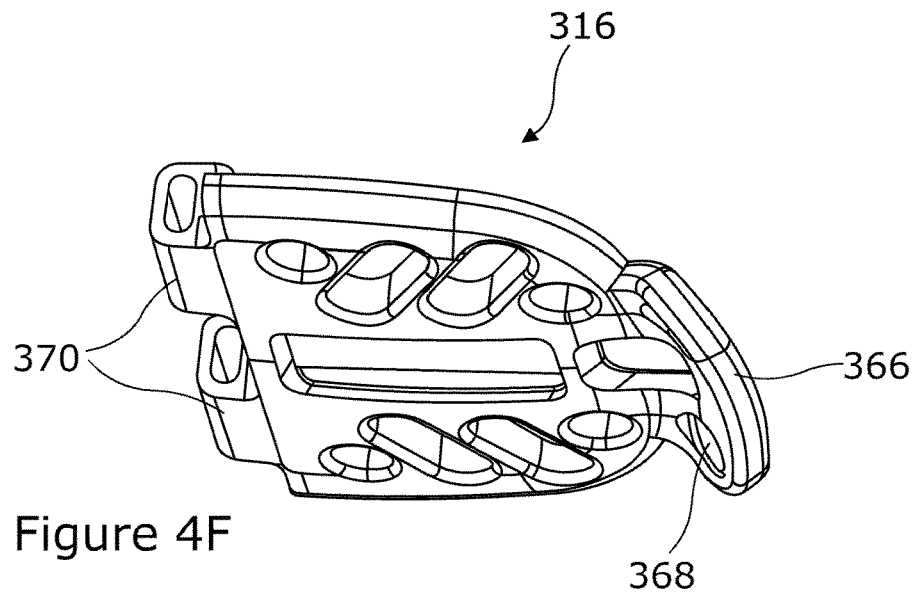
FIG. 4F is a perspective view from below of the inferior component of FIG. 4E.
Figure 4G:
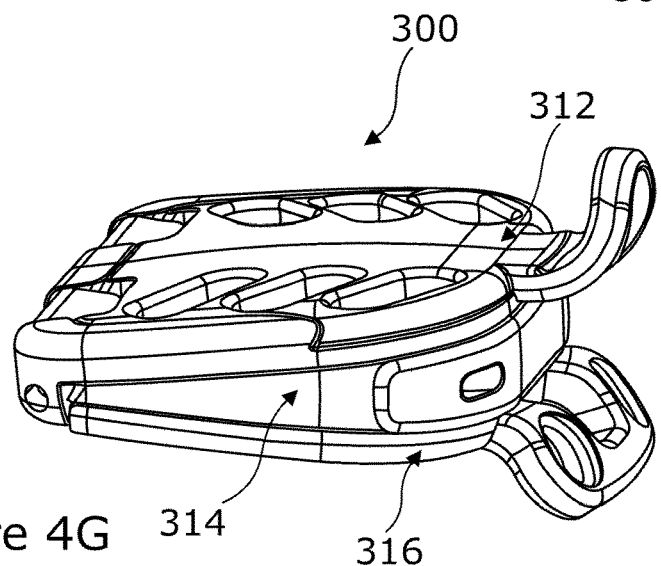
FIG. 4G is a perspective view from above of the fourth embodiment of anterior lumbar interbody fusion device when assembled and after correction of spondylolisthesis.

A fourth embodiment of anterior lumbar interbody fusion device 300 is shown in FIGS. 4A to 4G. As described above in respect of the first embodiment, the present embodiment of anterior lumbar interbody fusion (ALIF) device is introduced into a patient's intervertebral space between first and second adjacent vertebrae from the anterior side of the patient. The third embodiment of anterior lumbar interbody fusion device 300 comprises a superior component 312, a core component 314 and an inferior component 316. Perspective views of the superior component 312 from above and below are shown respectively in FIGS. 4A and 4B. Perspective views of the core component 314 from above and below are shown respectively in FIGS. 4C and 4D. Perspective views of the inferior component 316 from above and below are shown respectively in FIGS. 4E and 4F. FIG. 4G is a perspective view from above of the fourth embodiment of anterior lumbar interbody fusion device 300 when assembled and installed in an intervertebral space of a patient and after correction of spondylolisthesis.

As may be appreciated from inspection of FIGS. 4A to 4G, the fourth embodiment 300 is similar in structure to the third embodiment of anterior lumbar interbody fusion device 200.

Each of the superior component 312 (when assembled) and the inferior component 316 is generally of the form of a plate, albeit a plate having structures thereon and two spaced apart apertures therethrough. The core component 314 has the form of a frustum of a wedge. The anterior lumbar interbody fusion device 300 is assembled and installed in the intervertebral space by insertion of the inter-engaged superior and inferior components 312, 316 into the intervertebral space. The inferior component 316 is fixed with two screws to the lower or second vertebra either during the procedure or after correction of the spondylolisthesis. The core component 314 is then inserted between the already installed superior and inferior components. Then a part of the superior component 312 and the core component 314 are moved relative to the inferior component 316 such that the extent of overlap of the core and inferior components 314, 316 increases until the part of the superior component 312 is aligned with the upper or first vertebra. The surgeon then fixes the part of the superior component 312 with a screw to the upper vertebra. Alternatively, the screw fixing is done after correction of the spondylolisthesis. The surgeon then manipulates the patient to correct the spondylolisthesis with this involving further movement of the core component 314 in the posterior direction relative to the inferior component 316 by way of the screw threaded locking mechanism described below to increase the extent of overlap of the superior and inferior components until the spondylolisthesis is corrected. At this stage in the procedure, the fourth embodiment of anterior lumbar interbody fusion device 300 has the disposition shown in FIG. 4G.

Turning now to FIGS. 4A and 4B, the superior component 312 comprises first 313 and second 315 component parts, which are each integrally formed from a metal or plastics material. The first and second component parts 313, 315 inter-engage with each other such that the first component part moves relative to the second component part in the anterior-posterior direction. The second component part 315 defines two channels 317 each at a respective transverse side whereby the channels are spaced apart from and opposing each other. The first component part 313 defines first and second edges 319 at opposite transverse sides which are each shaped to be slidably received in a respective one of the two channels 317 whereby the first component part is constrained to move in the anterior-posterior direction relative to the second component.

The second component part 315 defines a first hinge structure 321 at its posterior end which interdigitates with a corresponding second hinge structure at the posterior end of the inferior component 316 with the first and second hinge structures being connected with a hinge pin (not shown) whereby the superior and inferior components are rotatably coupled to each other. The first and second hinge structures are configured to allow for a small amount of movement in the direction in which the superior and inferior components are spaced apart as well as for rotation. The first component part 313 has an integrally formed superior lug 322 which extends from an anterior end of the superior component and substantially orthogonally to the top side of the superior component such that the superior lug extends above the superior component top side. The superior lug 322 defines a superior lug aperture 324 extending therethrough. In use, the first component part 313 abuts against the upper vertebra. The first component part 313 is fixed to the upper vertebra by way of a screw and the superior lug aperture 324, as described above in respect of previous embodiments.

Referring now to FIG. 4B, the lower surface of the second component part 315 has an island 326 extending therefrom. The island 326 is of rectangular outline when viewed in plan and extends in the anterior-posterior direction. A threaded bolt 328 threadedly engages with a threaded bore defined in the island 326. Two projections 330, which are spaced apart in the transverse direction, project from the lower surface of the first component part 313 towards the second component part 315. The second component part 315 defines two parallel elongate apertures 332 which extend therethrough and in the anterior-posterior direction. The two parallel elongate apertures 332 are spaced apart in the transverse direction by a distance corresponding to the spacing apart of the two projections 330. When the first and second component parts 313 and 315 are slidably inter-engaged, as described above, each of the two projections 330 extends through a respective one of the two elongate apertures 332 and such that the projections 330 travel along the elongate apertures 332 as the first component part 313 moves linearly in relation to the second component part 315. As described further below, the distal ends of the two projections 330 abut against a posterior end of the core component 314 whereby movement of the core component in the posterior direction moves the two projections 330 in the posterior direction. The two projections 330 thus mechanically couple the core component 314 to the first component part 313 whereby the core component and the first component part move together in the posterior direction.

Turning now to FIGS. 4C and 4D, the core component 314 is integrally formed from a metal or plastics material. As can be seen from FIG. 4D, the upper and lower sides of the core component 314 are inclined to each other and do not meet at an acute angle whereby the core component has the form of a frustum of a wedge with the thickest part of the wedge at the anterior side of the core component. The anterior end of the core component 314 defines a core bore 334 extending in the anterior-posterior direction. The core component 314 also defines an elongate aperture 336, which is open at the upper and lower sides and at the posterior end of the core component, and which extends in the elongate anterior-posterior direction to a boundary wall near the anterior end. The core bore 334 extends through the boundary wall. The elongate aperture 336 and the island 326 are shaped and sized such that the island is progressively received in the elongate aperture as the core component moves in the posterior direction relative to the second component part 315. The threaded bolt 328 is received through the core bore 334 and threadedly engages with the threaded bore defined in the island 326. Rotation and resulting linear translation of the threaded bolt 328 causes the head of the threaded bolt to bear against the core component 314 to thereby move the core component in the posterior direction. Opposing sides of the elongate aperture 336 define respective shoulders 323 which face in the posterior direction. Each of the two projections 330 described above bears against a respective one of the shoulders 323 whereby movement of the core component causes corresponding movement of the first component part 313. The threaded bolt 328 is thus used to move the first component part 313 in the posterior direction to reduce the extent of spondylolisthesis.

The inferior component 316 of the fourth embodiment is shown in FIGS. 4E and 4F. The inferior component 316 is integrally formed from a metal or plastics material. The inferior component 316 is of a size such that it can be received in the intervertebral space whereby the bottom side of the inferior component abuts against the lower vertebra. The inferior component 316 has an integrally formed inferior lug 366 which extends from an anterior end of the inferior component and substantially orthogonally to the bottom side of the inferior component such that the inferior lug extends above the bottom side. The inferior lug 366 defines two inferior lug apertures 368 extending therethrough. The two inferior lug apertures 368 are spaced apart in the transverse direction. The inferior component 316 defines a second hinge structure 370 at its posterior end which interdigitates with the corresponding first hinge structure 321 at the posterior end of the second component part 315 with the first and second hinge structures being connected with a hinge pin (not shown) whereby the superior and inferior components are rotatably coupled to each other. As described above, the surgeon aligns the inferior component 316 with the lower vertebra and fixes the inferior component 316 to the lower vertebra with screws either during the procedure or after correction of the spondylolisthesis. Considering this part of the surgical procedure further, the inferior component 316 is aligned with the lower vertebra by moving the inferior component 316 in the intervertebral space in the posterior direction until the inferior lug 366 abuts against the anterior aspect of the lower vertebra. The surgeon drives a screw through each of the two inferior lug apertures 368 and into the lower vertebra to fix the inferior component 316 to the lower vertebra.

The fourth embodiment of anterior lumbar interbody fusion device 300 has dimensions appropriate for use as such. The first superior component has a range of length by width from 20 mm by 20 mm to 50 mm by 50 mm. The first superior component has a range of height at the posterior end from 1 mm to 4 mm. The second superior component has a range of length by width from 20 mm by 20 mm to 50 mm by 50 mm. The second superior component has a range of height at the posterior end from 1 mm to 4 mm. The inferior component has a range of length by width from 20 mm by 20 mm to 50 mm by 50 mm. The inferior component has a range of height at the posterior end from 1 mm to 4 mm. The core component has a range of length by width from 20 mm by 20 mm to 50 mm by 50 mm. The core component has a range of height at the posterior end from 4 mm to 10 mm.

The invention claimed is:

1. An anterior lumbar interbody fusion device for correcting spondylolisthesis when received in an intervertebral space between first and second vertebrae, the anterior lumbar interbody fusion device comprising:
   a superior component having a superior component top side and a superior component bottom side, the superior component configured to be received in the intervertebral space whereby the superior component top side abuts against the first vertebra;
   an inferior component having an inferior component top side and an inferior component bottom side, the inferior component configured to be received in the intervertebral space whereby the inferior component bottom side abuts against the second vertebra, the superior component bottom side and the inferior component top side opposing each other when the superior and inferior components are received in the intervertebral space; and
   a locking mechanism, wherein
   the superior and inferior components inter-engage with each other whereby: the inferior component is constrained to move in an anterior-posterior direction relative to the superior component; and resistance is presented to movement of the inferior component relative to the superior component in each of a direction of separation of the superior and inferior components and a transverse direction,
   each of the superior and inferior components is configured to engage with its respective vertebra whereby force is coupled between the superior and inferior components and their respective vertebra,
   the locking mechanism allows for relative movement of the inferior component in the anterior-posterior direction which increases an extent of overlap of the superior and inferior components and presents resistance to relative movement of the inferior component in the anterior-posterior direction which decreases the extent of overlap of the superior and inferior components, and
   the locking mechanism comprises a set of recesses which are spaced apart along the anterior-posterior direction and a sprung cantilever beam comprised in the inferior component and extending in the anterior-posterior direction, a protrusion which is shaped to be received under spring bias of the sprung cantilever beam in each recess of the set of recesses and which protrudes in the transverse direction from the cantilever beam, the protrusion moving from being received in one recess of the set of recesses to being received in an adjacent recess of the set of recesses as the extent of overlap between the superior and inferior components changes.

2. The anterior lumbar interbody fusion device according to claim 1 in which each of the superior and inferior components is shaped to abut against an aspect of the respective vertebra facing in the anterior-posterior direction to thereby engage with the respective vertebra.

3. The anterior lumbar interbody fusion device according to claim 1 in which each of the superior and inferior components comprises protruding teeth to thereby engage with the respective vertebra.

4. The anterior lumbar interbody fusion device according to claim 1 in which each of the superior and inferior components defines at its anterior end at least one aperture for receiving a fixing member for fixing to the respective vertebra to thereby engage with the respective vertebra.

5. The anterior lumbar interbody fusion device according to claim 1 in which the anterior lumbar interbody fusion device lacks a core component which is received between the superior and inferior components to thereby determine a separation between the superior and inferior components, and in which the superior and inferior components inter-engage directly with each other.

6. The anterior lumbar interbody fusion device according to claim 5 in which the inferior component comprises first and second channels which extend in the anterior-posterior direction, are spaced apart from each other in the transverse direction and face each other, and in which the superior component comprises first and second protrusions which extend along their length in the anterior-posterior direction, are spaced apart from each other in the transverse direction and face away from each other, the first and second protrusions slidably received in the first and second channels respectively to thereby change the extent of overlap between the superior and inferior components while presenting resistance to movement of the superior and inferior components relative to each other in each of a direction of separation of the superior and inferior components and the transverse direction.

7. The anterior lumbar interbody fusion device according to claim 1, in which the anterior lumbar interbody fusion device comprises a core component which is received between the superior and inferior components to thereby determine a separation between the superior and inferior components, and in which the core component inter-engages with each of the superior and inferior components whereby the superior and inferior components inter-engage indirectly with each other.

8. The anterior lumbar interbody fusion device according to claim 7 in which the inferior component comprises first and second channels which extend in the anterior-posterior direction, are spaced apart from each other in the transverse direction and face each other, and in which the core component comprises first and second protrusions which extend along their length in the anterior-posterior direction, are spaced apart from each other in the transverse direction and face away from each other, the first and second protrusions slidably received in the first and second channels respectively to thereby change the extent of overlap between the core component and the inferior component while presenting resistance to movement of the core and inferior components relative to each other in each of a direction of separation of the superior and inferior components and the transverse direction.

9. The anterior lumbar interbody fusion device according to claim 1 in which each recess of the set of recesses and the protrusion are shaped to engage with each other such that the set of recesses and the sprung cantilever beam form a ratchet whereby movement of the superior component relative to the inferior component is allowed in the posterior direction and is resisted in the anterior direction.

10. The anterior lumbar interbody fusion device according to claim 1 in which the locking mechanism comprises first and second sets of recesses, the first and second sets of recesses spaced apart from each other in the transverse direction and facing each other, the locking mechanism further comprising first and second cantilever beams spaced apart in the transverse direction on the inferior component with their respective protrusions facing in opposite directions, the protrusion of the first cantilever beam received in the first set of recesses and the protrusion of the second cantilever beam received in the second set of recesses.

11. The anterior lumbar interbody fusion device according to claim 1 and where the anterior lumbar interbody fusion device further comprises a core component received between the superior and inferior components, in which the set of recesses are comprised in the core component.

12. The anterior lumbar interbody fusion device according to claim 1 and where the anterior lumbar interbody fusion device comprises no core component received between the superior and inferior components, in which the set of recesses are comprised in the superior component.

13. The anterior lumbar interbody fusion device according to claim 1 and where the anterior lumbar interbody fusion device further comprises a core component received between the superior and inferior components, the anterior lumbar interbody fusion device further comprising a second locking mechanism which is operative to present a barrier to relative movement of the core and superior components in the anterior-posterior direction which decreases the extent of overlap of the core and superior components and only when the core and superior components are substantially fully overlapping.

14. The anterior lumbar interbody fusion device according to claim 13, in which the second locking mechanism is disengaged before the core component and the superior component are substantially fully overlapping whereby there is no barrier to relative movement of the core component and the superior component in the anterior-posterior direction, and is engaged only when the core component and the superior component are substantially fully overlapping to thereby present the barrier to relative movement of the core component and the superior component in the extent of overlap decreasing direction.

15. The anterior lumbar interbody fusion device according to claim 13, in which the second locking mechanism comprises a recess defined towards an anterior end of the core component and a sprung cantilever beam comprised in the superior component and extending in the anterior-posterior direction, there being no more than one recess along any one line between the anterior end and a posterior end of the core component, the sprung cantilever beam comprising a protrusion which protrudes in the transverse direction from the cantilever beam and which is shaped to be received in the recess under spring bias of the sprung cantilever beam when the core component and the superior component are substantially fully overlapping.

16. The anterior lumbar interbody fusion device according to claim 1, in which the cantilever beam is adjacent a line which bisects the inferior component and which extends in the anterior-posterior direction.

17. An anterior lumbar interbody fusion device for correcting spondylolisthesis when received in an intervertebral space between first and second vertebrae, the anterior lumbar interbody fusion device comprising:
    a superior component having a superior component top side and a superior component bottom side, the superior component configured to be received in the intervertebral space whereby the superior component top side abuts against the first vertebra;
    an inferior component having an inferior component top side and an inferior component bottom side, the inferior component configured to be received in the intervertebral space whereby the inferior component bottom side abuts against the second vertebra, the superior component bottom side and the inferior component top side opposing each other when the superior and inferior components are received in the intervertebral space;
    a core component which is received between the superior and inferior components to thereby determine a separation between the superior and inferior components, and in which the core component inter-engages with each of the superior and inferior components; and
    a locking mechanism, wherein
    the superior and inferior components inter-engage with each other whereby: one of the superior and inferior components is constrained to move in an anterior-posterior direction relative to another of the superior and inferior components; and resistance is presented to movement of the one of the superior and inferior components relative to the other of the superior and inferior components in each of a direction of separation of the superior and inferior components and a transverse direction,
    each of the superior and inferior components is configured to engage with its respective vertebra whereby force is coupled between the superior and inferior components and their respective vertebra,
    the locking mechanism allows for movement of the one of the superior and inferior components in the anterior-posterior direction which increases an extent of overlap of the superior and inferior components and presents resistance to movement of the one of the superior and inferior components in the anterior-posterior direction which decreases the extent of overlap of the superior and inferior components, the superior component defines at least one superior component profile and the core component defines at least one core component profile, the at least one superior component profile and the at least one core component profile shaped to cooperate with each other when the core component is moved in the anterior-posterior direction relative to the superior component to present a barrier to relative movement of the superior and core components in the transverse direction, the at least one superior component profile and the at least one core component profile further shaped to present no barrier to relative movement of the superior and core components in the direction of separation of the superior and inferior components when the superior and core components are no more than substantially half overlapping each other, and the at least one superior component profile and the at least one core component profile further shaped to present a second barrier to relative movement of the superior and core components in the direction of separation of the superior and inferior components when the superior and core components are more than substantially half overlapping each other, and the superior component defines first and second superior planar surfaces which extend in the anterior-posterior direction, are spaced apart from each other in the transverse direction and face each other, and in which the core component defines first and second core planar surfaces which extend in the anterior-posterior direction, are spaced apart from each other in the transverse direction and face away from each other, the first and second core planar surfaces received between the first and second superior planar surfaces and slidably moving relative to the first and second superior planar surfaces when the extent of overlap of superior and core components changes.

18. An anterior lumbar interbody fusion device for correcting spondylolisthesis when received in an intervertebral space between first and second vertebrae, the anterior lumbar interbody fusion device comprising:

a superior component having a superior component top side and a superior component bottom side, the superior component configured to be received in the intervertebral space whereby the superior component top side abuts against the first vertebra;

an inferior component having an inferior component top side and an inferior component bottom side, the inferior component configured to be received in the intervertebral space whereby the inferior component bottom side abuts against the second vertebra, the superior component bottom side and the inferior component top side opposing each other when the superior and inferior components are received in the intervertebral space;

a core component received between the superior and inferior components; and first and second locking mechanisms, wherein the superior and inferior components inter-engage with each other whereby: the superior and inferior components are constrained to move in an anterior-posterior direction relative to each other; and resistance is presented to movement of the inferior component relative to the superior component in each of a direction of separation of the superior and inferior components and a transverse direction, each of the superior and inferior components is configured to engage with its respective vertebra whereby force is coupled between the superior and inferior components and their respective vertebra, the first locking mechanism allows for relative movement of the inferior component in the anterior-posterior direction which increases an extent of overlap of the superior and inferior components and presents resistance to relative movement of the inferior component in the anterior-posterior direction which decreases the extent of overlap of the superior and inferior components, the second locking mechanism is operative to present a barrier to relative movement of the core and superior components in the anterior-posterior direction which decreases the extent of overlap of the core and superior components and only when the core and superior components are substantially fully overlapping, and the second locking mechanism comprises a recess defined towards an anterior end of the core component and a sprung cantilever beam comprised in the superior component and extending in the anterior-posterior direction, the sprung cantilever beam comprising a protrusion which is shaped to be received under spring bias of the sprung cantilever beam in the recess and which protrudes in the transverse direction from the cantilever beam.

19. The anterior lumbar interbody fusion device according to claim 18 in which the second locking mechanism comprises first and second recesses defined by the core component and first and second sprung cantilever beams comprised in the superior component, each of the first and second sprung cantilever beams comprising a protrusion, the first and second recesses spaced apart in the transverse direction and facing each other, the protrusions of the first and second sprung cantilever beams spaced apart in the transverse direction and facing away from each other, each of the protrusions of the first and second sprung cantilever beams received in a respective one of the first and second recesses.

20. A method of correcting spondylolisthesis with an anterior lumbar interbody fusion device, the anterior lumbar interbody fusion device receivable in an intervertebral space between first and second vertebrae and comprising a superior component, an inferior component and a locking mechanism, the method comprising:

receiving the superior component in the intervertebral space, the superior component having a superior component top side and a superior component bottom side, the superior component top side abutting against the first vertebra;

receiving the inferior component in the intervertebral space, the inferior component having an inferior component top side and an inferior component bottom side, the inferior component bottom side abutting against the second vertebra, the superior component bottom side and the inferior component top side opposing each other when the superior and inferior components are received in the intervertebral space;

bringing the superior and inferior components into inter-engagement with each other whereby: the inferior component is constrained to move in an anterior-posterior direction relative to the superior component; and resistance is presented to movement of the inferior component relative to the superior component in each of a direction of separation of the superior and inferior components and a transverse direction, each of the superior and inferior components configured to engage with its respective vertebra whereby force is coupled between the superior and inferior components and their respective vertebra; and relatively moving the inferior component in the anterior-posterior direction which increases an extent of overlap of the superior and inferior components, the locking mechanism allowing said extent of overlap increasing relative movement but presenting resistance to relative movement of the inferior component in the anterior-posterior direction which decreases the extent of overlap of the superior and inferior components, wherein the locking mechanism comprises a set of recesses which are spaced apart along the anterior-posterior direction and a sprung cantilever beam comprised in the inferior component and extending in the anterior-posterior direction, a protrusion which is shaped to be received under spring bias of the sprung cantilever beam in each recess of the set of recesses and which protrudes in the transverse direction from the cantilever beam, the protrusion moving from being received in one recess of the set of recesses to being received in an adjacent recess of the set of recesses as the extent of overlap between the superior and inferior components changes.

* * * * *